United States Patent [19]

Curran et al.

[11] Patent Number: 6,008,196

[45] Date of Patent: *Dec. 28, 1999

[54] PERFLUOROALKYL KETONE INHIBITORS OF ELASTASE AND PROCESSES FOR MAKING THE SAME

[75] Inventors: Timothy T. Curran, Chester, N.Y.; Joseph P. Burkhart, Plainfield, Ind.; Michael R. Angelastro, Mason, Ohio; Norton P. Peet, Cincinnati, Ohio; William A. Metz, Jr., Loveland, Ohio

[73] Assignee: Hoechst Marion Roussel, Inc., Bridgewater, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 08/737,905

[22] PCT Filed: May 1, 1995

[86] PCT No.: PCT/US95/05363

§ 371 Date: Nov. 22, 1996

§ 102(e) Date: Nov. 22, 1996

[87] PCT Pub. No.: WO95/33762

PCT Pub. Date: Dec. 14, 1995

Related U.S. Application Data

[63] Continuation of application No. 08/327,520, Oct. 20, 1994, Pat. No. 5,403,052, which is a continuation-in-part of application No. 08/252,857, Jun. 2, 1994, abandoned.

[51] Int. Cl.$^6$ .......................... A61K 38/06; A61K 38/07; C07K 5/08; C07K 5/10
[52] U.S. Cl. ............................. 514/18; 530/330; 530/331
[58] Field of Search .................................... 530/330–331; 514/18

[56] References Cited

U.S. PATENT DOCUMENTS

| | | |
|---|---|---|
| 4,277,395 | 7/1981 | Bey et al. . |
| 4,518,528 | 5/1985 | Rasnick . |
| 4,623,639 | 11/1986 | Hassall et al. . |
| 4,629,724 | 12/1986 | Ryono et al. . |
| 4,636,489 | 1/1987 | Seemuller et al. . |
| 4,643,991 | 2/1987 | Digenis et al. . |
| 4,855,303 | 8/1989 | Hoover . |
| 4,873,221 | 10/1989 | Trainor . |
| 4,880,780 | 11/1989 | Trainor et al. . |
| 4,910,190 | 3/1990 | Bergeson et al. . |
| 4,935,405 | 6/1990 | Hoover et al. . |
| 5,055,450 | 10/1991 | Edwards et al. . |
| 5,114,927 | 5/1992 | Schirlin . |
| 5,162,307 | 11/1992 | Digenis et al. . |
| 5,221,665 | 6/1993 | Skiles ........................................ 514/18 |
| 5,478,811 | 12/1995 | Peet et al. ................................. 514/17 |
| 5,496,927 | 3/1996 | Kolb et al. ............................... 530/328 |
| 5,510,333 | 4/1996 | Angelastro et al. ....................... 514/18 |

FOREIGN PATENT DOCUMENTS

| | | |
|---|---|---|
| 0009384 | 4/1980 | European Pat. Off. . |
| 0189305 | 7/1986 | European Pat. Off. . |
| 0195212 | 9/1986 | European Pat. Off. . |
| 0204571 | 12/1986 | European Pat. Off. . |
| 0318318 | 5/1989 | European Pat. Off. . |
| 0369391 | 5/1990 | European Pat. Off. . |
| 0410411 | 1/1991 | European Pat. Off. . |
| 0494071 | 7/1992 | European Pat. Off. . |
| 0529568 | 3/1993 | European Pat. Off. . |
| 9113904 | 9/1991 | WIPO . |
| 9115487 | 10/1991 | WIPO . |
| 9212140 | 8/1992 | WIPO . |
| 9215605 | 9/1992 | WIPO . |
| 9509838 | 4/1995 | WIPO . |
| 9533478 | 12/1995 | WIPO . |
| 9533762 | 12/1995 | WIPO . |
| 9533763 | 12/1995 | WIPO . |

OTHER PUBLICATIONS

Sham et al, FEB 05016, vol. 220, No. 2, pp. 299–301 (1987).
Travis et al, Am. Rev. Respir, Dis. 143: 1412–1415, (1991).
Eleventh American Peptide Symposium—Jul. 9–14, 1989.
Petrillo et al, Annual Reports in Medicinal Chemistry 25, pp. 51–60.
Chemical Abstracts.
Mehdi et al, Biochemical and Biophysical Research Communications, vol. 166, No. 2, pp. 595–600 (1990).
M.R. Angelastro et al., Bioorganic & Medicinal Chem Let, vol. 3, No. 4 pp. 525–530, (1993).
Peet et al, J. Med. Chem. 33, pp. 394–407 (1990).
Durham et al, J. Pharm. Exp. Ther., vol. 270, No. 1, pp. 185–191 (1994).
Imperiali et al, Biochemistry 25, 3760–3767, (1986).
Skiles et al, Journal of Medicinal Chemistry, vol. 35, No. 4, pp. 641–661 (1992).
Repine et al, J. Med Chem. 34, pp. 1935–1943 (1991).
Ueda et al, Biochem. J. 265 pp. 539–545 (1990).
Steinmeyer et al, Forsch./Drug Res. 41, (l) Nr. (1991).
McWherter et al, Biochemistry 28, pp. 5708–5713 (1989).
Reilly et al, Biochemica et Biophysica Acta. 621 pp. 147–157, (1980).
Najajima et al, Journal of Biological Chemistry, vol. 254, pp. 4027–4031 (1979).
Rice et al, Science, vol. 249, pp. 178–181.
Travis, The American Journal of Medicine, vol. 84, Supl 6A pp. 37–42 (1988).
M.R. Angelastro et al., J. Org. Chem. vol. 54, pp. 3913–3916, (1989).
S. Mehdi, Biogorganic Chem., vol. 21, pp. 249–259, (1993).
M.R. Angelastro et al., Tetrahedron Let, vol. 33, No. 23, pp. 3265–3268, (1992).

(List continued on next page.)

*Primary Examiner*—Bennett Celsa
*Attorney, Agent, or Firm*—Balaram Gupta

[57] ABSTRACT

This invention relates to compounds which are inhibitors of elastase, particularly human neutrophil elastase, and to novel processes for making the same. As inhibitors of human neutrophil elastase, the compounds are useful in the treatment of a patient afflicted with a neutrophil associated inflammatory disease.

9 Claims, No Drawings

OTHER PUBLICATIONS

J.P. Burkhart et al., Tetrahedron Let, vol. 31, No. 10, pp. 1385–1388, (1990).

Doherty et al, Int. J. Immunopharmac vol. No. 7, pp. 787–795, (1990).

Shah et al, pp. 3745–3754.

Snider, Eur, J. Respir. 69, suppl 146, 17–35, (1986).

Malech et al, Medical Intellegence vol. 317, No. 11, pp. 687–694.

Fletcher et al, Am Rev Respir Dis 1990, 141:672–677.

Hassall et al, Febs 2444, vol. 183, No. 2, (1985).

Mehdi et al., Biochem. & Biophy. Res. Comm., vol. 166, No. 2, pp. 595–600, (1990).

P.G. Gassman et al., J. Org. Chem. vol. 52, pp. 2481–2490, (1987).

Skiles et al., J. Med. Chem. 1992, 35, pp. 641–662, Inhibition of Human Leukocyte Elastase (HLE) by N–Substituted Peptidyl Trifluoromethyl Ketones1.

Skiles et al., J. Med. Chem. 1992, 35, pp. 4795–4808, Inhibition of Human Leukocyte Elastase by N–Substituted Peptides Containing alpha, alpha–Difluorostatone Residues at P1.

Williams et al., Am. Rev. Respir. Dis. 1991; 144; pp. 875–993.

Kawase et al., Tetahedron Letters, vol. 34, No. 5 pp. 859–862, 1993, "Unexpected Product from the Dakin–West Reaction of N–Acylprolines using Trifluoroacetic Anhydride: A Novel Access to 5– Trifluoromethyl–oxazoles".

Kawase, J. Chem. Soc., Chem. Commun., 1992, pp. 1076–1077, "Unusual Ring Expansion observed during the Dakin–West Reaction of Tetrahydroisoquinoline–1–carboxylic Acids using Trifluoroacetic Anhydride: an Expedient Synthesis of 3–Benzazepine Derivatives bearing a Trifluoromethyl Group".

Bundgaard, Hans, Bioreversible Carriers In Drug Design Theory and Appl., pp. 13, 63–65 (1987).

Powers, J.C., Eleventh American paptide Symposium, Abstracts, The Salk Institute and U. of CA, San Diego (1989) Internal notes taken at meeting.

Angelastro et al, Bioorganic & Medicinal Chemistry Letters, vol. 2, No. 10, pp. 1235–1238 (1992).

Angelastro et al, J. Med. Chem. 33, "Communications to the Editor" pp. 11–13 (1990).

Burkhart et al, J. med. Chem., 38, pp. 223–233 (1995).

Travis et al, Am. Rev. Respir., Dis. 143:1412–1415 (1991).

M.R. Angelastro et al., J. Med. Chem. vol. 37, pp. 4538–4554 (1994).

Janusz, M. et al, J. Immonol. (1991), vol. 146, pp. 3922–3928.

Janusz, M. et al, J. Pharmacol. Exp. Ther., (1995), vol. 275, pp. 1233–1238.

PERFLUOROALKYL KETONE INHIBITORS OF ELASTASE AND PROCESSES FOR MAKING THE SAME

This application is a national stage entry under 35 U.S.C. § 371 of an International Application No. PCT/US95/05363, filed May 1, 1995, which claims the benefit of priority of U.S. application Ser. No. 08/327,520, filed Oct. 20, 1994, now U.S. Pat. No. 5,403,052; which is a continuation-in-part application of U.S. application Ser. No. 08/252,857, filed Jun. 2, 1994, now abandoned.

BACKGROUND OF THE INVENTION

This invention relates to compounds which are inhibitors of elastase, particularly human neutrophil elastase, useful for a variety of physiological and end-use applications, and to processes for making said inhibitors.

Human neutrophil elastase has been implicated as an agent contributing to the tissue destruction associated with a number of inflammatory diseases such as chronic bronchitis, cystic fibrosis, and rheumatoid arthritis. J. L. Malech and J. I. Gallin, *New Engl. J. Med.,* 317(11), 687 (1987). Elastase possesses a broad range of proteolytic activity against a number of connective tissue macromolecules including elastin, fibronectin, collagen, and proteoglycan. The presence of the enzyme elastase may contribute tc the pathology of these diseases.

Normal plasma contains large quantities of protease inhibitors that control a variety of enzymes involved in connective tissue turnover and inflammation. For example, α-1-proteinase inhibitor (α-1-$P_1$) is a serine protease inhibitor that blocks the activity of elastase. α-1-$P_1$ has received considerable interest because reduction in plasma levels to less than 15% of normal is associated with the early development of emphysema. In addition to plasma derived protease inhibitors, secretory fluids, including bronchial, nasal, cervical mucus, and seminal fluid contain an endogenous protease inhibitor called secretory leukoprotease inhibitor ($SLP_1$) that can inactivate elastase and is believed to play an important role in maintaining the integrity of the epithelium in the presence of inflammatory cell proteases. In certain pathological states α-1-$P_1$ and $SLP_1$ are inactivated by neutrophil oxidative mechanisms allowing the neutrophil proteases to function in an essentially inhibitor-free environment. For example, bronchial lavage fluids from patients with adult respiratory distress syndrome (ARDS) have been found to contain active elastase and α-1-$P_1$ that had been inactivated by oxidation.

In addition to oxidative mechanisms, neutrophils possess non-oxidative mechanisms for eluding inhibition by antiproteases. Neutrophils from patients with chronic granulomatous disease are capable of degrading endothelial cell matrices in the presence of excess α-1-$P_1$. There is considerable in vitro evidence that stimulated neutrophils can tightly bind to their substrates such that serum antiproteases are effectively excluded from the microenvironment of tight cell-substrate contact. The influx of large numbers of neutrophils to an inflammatory site may result in considerable tissue damage due to the proteolysis that occurs in this region.

Applicants have determined that elastase is one of the primary neutrophil proteases responsible for cartilage matrix degeneration as measured by the ability of neutrophil lysate, purified elastase and stimulated neutrophils to degrade cartilage matrix proteoglycan. Furthermore, applicants have previously discovered peptide derivatives useful as elastase inhibitors, exerting valuable pharmacological activities. For example, peptide derivatives useful as elastase inhibitors wherein the terminal carboxyl group has been replaced by a pentafluoroethylcarbonyl (—C(O)$C_2F_5$)group and in which the N-terminal amino acid is substituted with various protecting groups are disclosed in European Patent Application OPI No. 0529568, inventors Peet et al., with a publication date of Mar. 3, 1993 and European Patent Application OPI No. 0410411, inventors Bey et al., with a publication date of Jan. 30, 1991. Because of new processes for making perfluoroalkylcarbonyl peptides, Applicants have recently discovered heptafluoropropylcarbonyl and nonaflurobutylcarbonyl moieties of elastase inhibitors.

SUMMARY OF THE INVENTION

The present invention relates to compounds having the following formula I

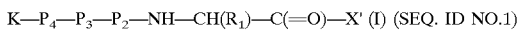

or a hydrate, isostere, or pharmaceutically acceptable salt thereof wherein $P_4$ is Ala, bAla, Leu, Ile, Val, Nva, bVal, Nle or a bond;
$P_3$ is Ala, bAla, Leu, Ile, Val, Nva, bVal, Nle or an N-methyl derivative, Pro, Ind, Tic or Tca, or Lys substituted on its epsilon amino group with a morpholino-B-group or Orn substituted on its delta amino group with a morpholino-B-group;
$P_2$ is Pro, Ind, Tic, Pip, Tca, Pro(4-OBzl), Aze, Pro(4-OAc) or Pro(4-OH);
$R_1$ is a side chain of Ala, Leu, Ile, Val, Nva or bVal;
X' is —$CF_2CF_2CF_3$ or —$CF_2CF_2CF_2CF_3$;
K is hydrogen, formyl, acetyl, succinyl, benzoyl, t-butyloxycarbonyl, carbobenzyloxy, tosyl, dansyl, isovaleryl, methoxysuccinyl, 1-adamantanesulphonyl, 1-adamantaneacetyl, 2-carboxybenzoyl, phenylacetyl, t-butylacetyl, bis((1-naphthyl)methyl)acetyl,

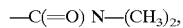

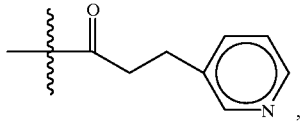

—A—$R_z$ wherein

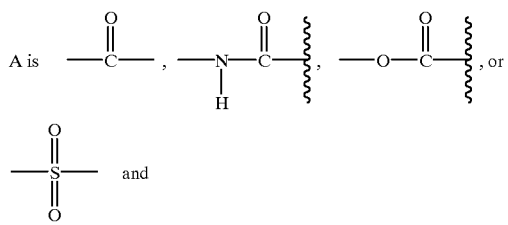

$R_z$ is an aryl group containing 6, 10 or 12 carbons suitably substituted by 1 to 3 members selected independently from the group consisting of fluoro, chloro, bromo, iodo, trifluoromethyl, hydroxy, alkyl containing from 1 to 6 carbons, alkoxy containing from 1 to 6 carbons, carboxy, alkylcarbonylamino wherein the alkyl group contains 1 to 6 carbons, 5-tetrazolyl, and acylsulfonamido containing from 1 to 15 carbons, provided that when the acylsulfonamido contains an aryl the aryl may be further substituted by a member selected from fluoro, chloro, bromo, iodo and nitro;

or

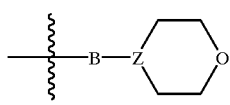

wherein
Z is N or CH, and
B is a group of the formulae

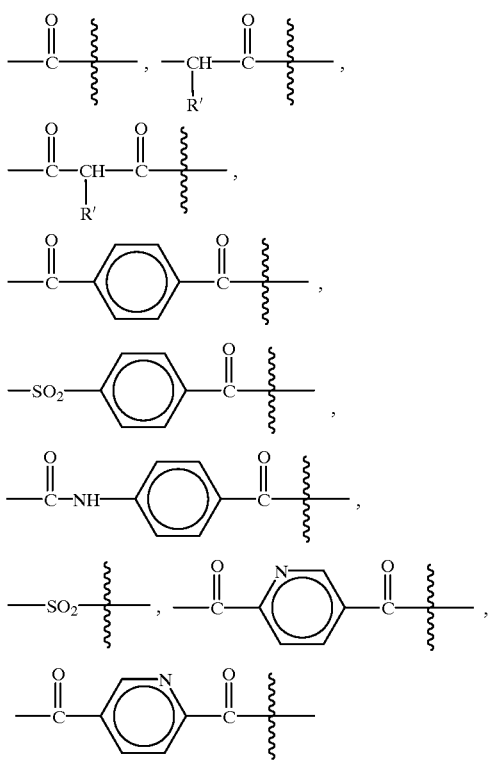

(the wavy line ⸱ being the attachment to the rest of the molecule, i.e., not to Z)
and wherein R' is hydrogen or a $C_{1-6}$ alkyl group; useful as inhibitors of elastase. The compounds of formula I exhibit an anti-inflammatory effect useful in the treatment of gout, rheumatoid arthritis and other inflammatory diseases, such as adult respiratory distress syndrome, septicemia, disseminated intravascular coagulation, cystic fibrosis, chronic bronchitis, chronic obstructive pulmonary disease, inflammatory bowel disease (particularly ulcerative colitis or Crohn's disease) and in the treatment of emphysema.

In a further embodiment the present invention provides a novel process for the preparation of a compound of the formula

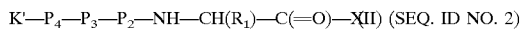

K'—P$_4$—P$_3$—P$_2$—NH—CH(R$_1$)—C(=O)—X(II) (SEQ. ID NO. 2)

wherein
P$_4$ is Ala, bAla, Leu, Ile, Val, Nva, bVal, Nle or a bond;
P$_3$ is Ala, bAla, Leu, Ile, Val, Nva, bVal, Nle or an N-methyl derivative, Pro, Ind, Tic or Tca, or Lys substituted on its epsilon amino group with a morpholino-B-group or Orn substituted on its delta amino group with a morpholino-B-group;
P$_2$ is Pro, Ind, Tic, Pip, Tca, Pro(4-OBzl), Aze, Pro(4-OAc) or Pro(4-OH);
R$_1$ is a side chain of Ala, Leu, Ile, Val, Nva or bVal;
X is —CF$_2$CF$_3$, —CF$_2$CF$_2$CF$_3$ or —CF$_2$CF$_2$CF$_2$CF$_3$;
K' is hydrogen, formyl, acetyl, succinyl, benzoyl, t-butyloxycarbonyl, carbobenzyloxy, tosyl, dansyl, isovaleryl, methoxysuccinyl, 1-adamantanesulphonyl, 1-adamantaneacetyl, 2-carboxybenzoyl, phenylacetyl, t-butylacetyl, bis((1-naphthyl)methyl)acetyl, —C(=O)N—(CH$_3$)$_2$,

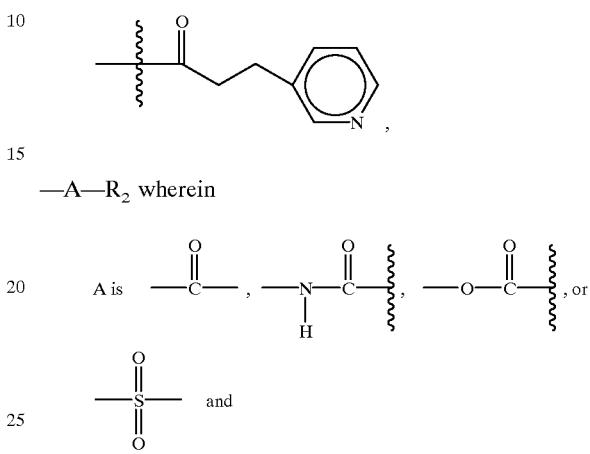

—A—R$_2$ wherein

A is 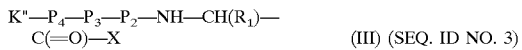

R$_z$ is an aryl group containing 6, 10 or 12 carbons suitably substituted by 1 to 3 members selected independently from the group consisting of fluoro, chloro, bromo, iodo, trifluoromethyl, hydroxy, alkyl containing from 1 to 6 carbons, alkoxy containing from i to 6 carbons, carboxy, alkylcarbonylamino wherein the alkyl group contains 1 to 6 carbons, 5-tetrazolyl, and acylsulfonamido containing from 1 to 15 carbons, provided that when the acylsulfonamido contains an aryl the aryl may be further substituted by a member selected from fluoro, chloro, bromo, iodo and nitro; comprising the steps of:

(a) coupling an amino acid ester of the formula NH$_2$-CH(R$_1$)C(=O)OR$_2$ wherein R$_2$ is (C$_{1-6}$)alkyl or (C$_{3-12}$)cycloalkyl, with a suitably N-protected peptide of the formula K'—P$_4$—P$_3$—P$_2$—OH in the presence of a suitable coupling agent and in the presence of an appropriate coupling solvent to give a suitably N-protected peptide ester;

(b) reacting the suitably N-protected peptide ester with a suitable perfluorinating agent in the presence of a suitable alkali metal base and an appropriate anhydrous solvent.

The present invention further provides a novel process for the preparation of a compound of the formula

K"—P$_4$—P$_3$—P$_2$—NH—CH(R$_1$)—
C(=O)—X         (III) (SEQ. ID NO. 3)

wherein
P$_4$ is Ala, bAla, Leu, Ile, Val, Nva, bVal, Nle or a bond;
P$_3$ is Ala, bAla, Leu, Ile, Val, Nva, bVal, Nle or an N-methyl derivative, Pro, Ind, Tic or Tca, or Lys substituted on its epsilon amino group with a morpholino-B-group or Orn substituted on its delta amino group with a morpholino-B-group;
P$_2$ is Pro, Ind, Tic, Pip, Tca, Pro(4-OBzl), Aze, Pro(4-OAc) or Pro(4-OH);
R$_1$ is a side chain of Ala, Leu, Ile, Val, Nva or bVal;
X is —CF$_2$CF$_3$, —CF$_2$CF$_2$CF$_3$ or —CF$_2$CF$_2$CF$_2$CF$_3$;
K" is or

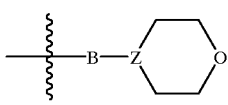

wherein
Z is N or CH, and
B is a group of the formulae

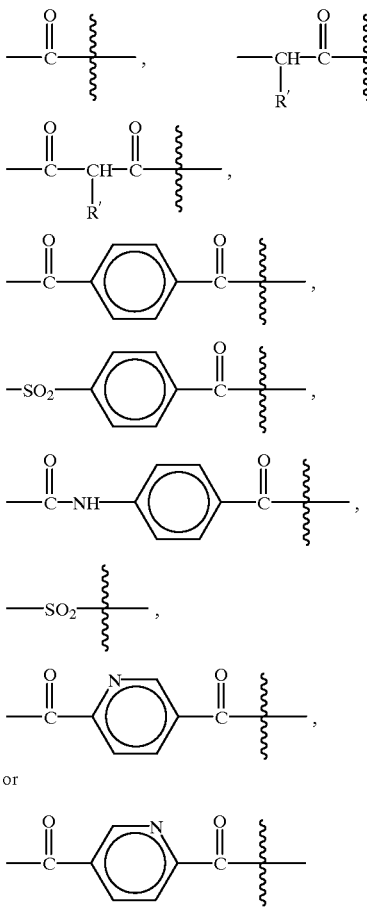

and wherein R' is hydrogen or a $C_{1-6}$ alkyl group; comprising the steps of:

(a) coupling an amino acid ester of the formula $NH_2$-CH$(R_1)C(=O)OR_2$ wherein $R_2$ is $(C_{1-6})$alkyl or $(C_{3-12})$cycloalkyl, with a suitably N-protected peptide of the formula K'—$P_4$—$P_3$—$P_2$—OH in the presence of a suitable coupling agent and in the presence of an appropriate coupling solvent to give a suitably N-protected peptide ester;

(b) reacting the suitably-N-protected peptide ester with a suitable perfluorinating agent in the presence of a suitable alkali metal base and an appropriate anhydrous solvent to give a suitably N-protected perfluroalkyl peptide;

(c) deprotecting the suitably N-protected perfluroalkyl peptide with a suitable deprotecting agent in the presence of an appropriate organic solvent to give a perfluoroalkyl peptide;

(d) reacting the perfluoroalkyl peptide with a compound of the formula

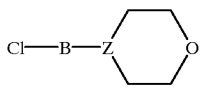

wherein B and Z are as defined above, in the presence of a suitable non-nucleophilic base and an appropriate organic solvent.

The present invention further provides a novel process for the preparation of a compound of formula (II), comprising the steps of:

(a) reacting a suitably protected amino acid ester of the formula Pg—NH—CH$(R_1)C(=O)OR_2$ wherein $R_2$ is $(C_{1-6})$alkyl or $(C_{3-12})$cycloalkyl and Pg is a suitable protecting group, with a suitable perfluorinating agent in the presence of a suitable alkali metal base and an appropriate anhydrous solvent to give a suitably N-protected perfluroalkyl ketone;

(b) deprotecting the suitably N-protected perfluroalkyl ketone with a suitable deprotecting agent in the presence of an appropriate organic solvent to give a perfluoroalkyl ketone;

(c) coupling the perfluoroalkyl ketone with a suitably protected peptide of the formula K'—$P_4$—$P_3$—$P_2$—OH in the presence of a suitable coupling agent and in the presence of an appropriate coupling solvent.

The present invention further provides a novel process for the preparation of a compound of formula (III), comprising the steps of:

(a) reacting a suitably protected amino acid ester of the formula Pg—NH—CH$(R_1)C(=O)OR_2$ wherein $R_2$ is $(C_{1-6})$alkyl or $(C_{3-12})$cycloalkyl and Pg is a suitable protecting group, with a suitable perfluorinating agent in the presence of a suitable alkali metal base and an appropriate anhydrous solvent to give a suitably N-protected perfluroalkyl ketone;

(b) deprotecting the suitably N-protected perfluroalkyl ketone with a suitable deprotecting agent in the presence of an appropriate organic solvent to give a perfluoroalkyl ketone;

(c) coupling the perfluoroalkyl ketone with a suitably protected peptide of the formula K"—$P_4$—$P_3$—$P_2$—OH in the presence of a suitable coupling agent and in the presence of an appropriate coupling solvent.

The present invention further provides novel compounds having the following formula (IV)

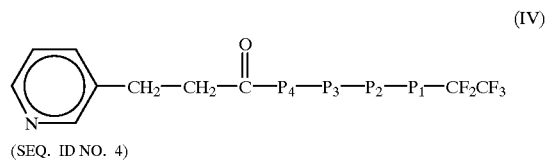

(SEQ. ID NO. 4)

wherein
$P_1$ is Ala, Val, Nva, bVal, Leu, Ile or Nle;
$P_2$ is Ala, bAla, Leu, Ile, Val, Nva, bVal, Met, Nle, Gly, Phe, Tyr, Trp, or Nal(1) where the nitrogen of the alpha-amino group can be substituted with an R group where R is a $(C_{1-6})$alkyl, $(C_{3-12})$cycloalkyl, $(C_{3-12})$cycloalkyl$(C_{1-6})$alkyl, $(C_{4-11})$bicycloalkyl, $(C_{4-11})$bicycloalkyl$(C_{1-6})$alkyl, $(C_{6-10})$aryl, $(C_{6-10})$aryl$(C_{1-6})$alkyl, $(C_{3-7})$heterocycloalkyl, $(C_{3-7})$heterocycloalkyl$(C_{1-6})$alkyl, $(C_{5-9})$heteroaryl, $(C_{5-9})$heteroaryl$(C_{1-6})$alkyl, fused $(C_{6-}$ 10)aryl-($C_{3-12}$)cycloalkyl, fused ($C_{6-10}$)aryl($C_{3-12}$)cycloalkyl($C_{1-6}$)alkyl, fused ($C_{5-9}$)heteroaryl($C_{3-12}$)cycloalkyl, or fused ($C_{5-9}$)heteroaryl($C_{3-12}$)cycloalkyl-($C_{1-6}$)alkyl, or $P_2$ is Pro, Ind, Tic or Tca;

$P_3$ is Ala, bAla, Leu, Ile, Val, Nva, bVal or Nle;

$P_4$ is Ala, bAla, Leu, Ile, Val, Nva, bVal, Nle or a bond; or a hydrate, isostere, or pharmaceutically acceptable salt thereof.

DETAILED DESCRIPTION OF THE INVENTION

Isosteres of the compounds of formulae (I)–(IV) include those wherein (a) one or more of the α-amino residues of the $P_2$—$P_4$ substituents are in its unnatural configuration (when there is a natural configuration) or (b) when the normal peptidic amide Linkage [—C(=O)NH—] is modified, such as for example, to form —$CH_2NH$— (reduced), —$COCH_2$— (keto), —CH(OH)$CH_2$— (hydroxy), —CH($NH_2$)$CH_2$— (amino), —$CH_2CH_2$— (hydrocarbon), —CH=CH— (alkene). Preferably a compound of the invention should not be in an isosteric form; particularly it is preferred that there be no modified peptidic amide group, but if there is, it is preferable to keep the isosteric modifications to a minimum.

As used herein the term "($C_{1-6}$)alkyl" means a straight or branched alkyl group of from 1 to 6 carbon atoms, such as, methyl, ethyl, n-propyl, isopropyl, n-butyl, tert-butyl, n-pentyl, sec-pentyl, iso-pentyl, and n-hexyl. The term "($C_{3-12}$)cycloalkyl." means a cyclic alkyl group consisting of a 3 to 8 member ring which can be substituted by a lower alkyl group, for example, cyclopropyl, cyclobutyl cyclopentyl, cyclohexyl, 4-methylcyclohexyl, 4-ethylcyclohexyl, cycloheptyl, and cyclooctyl. The term "($C_{3-12}$)cycloalkyl ($C_{1-6}$)alkyl" means a ($C_{1-6}$)alkyl group substituted by a ($C_{3-12}$)cycloalkyl group, such as a cyclohexylmethyl or cyclopentylethyl group. The term "($C_{4-11}$)bicycloalkyl" means an alkyl group containing one pair of bridgehead carbon atoms, such as 2-bicyclo[1.1.0]-butyl, 2-bicyclo[2.2.1]hexyl, and 1-bicyclo[2.2.2]octane. The term "($C_{4-11}$)bicycloalkyl($C_{1-6}$)alkyl" means a ($C_{1-6}$)alkyl substituted by a ($C_{4-11}$)bicycloalkyl, such as 2-bicyclohexylmethyl. The term "($C_{6-10}$)aryl" means a cyclic, aromatic assemblage of conjugated carbon atoms, for example, phenyl, 1-naphthyl, and 2-naphthyl. The term "($C_{6-10}$)aryl($C_{1-6}$)alkyl" means a ($C_{1-6}$)alkyl substituted by a ($C_{6-10}$)aryl, such as benzyl, phenethyl, and 1-naphthylmethyl. The term "($C_{3-7}$)heterocycloalkyl" means a nonaromatic, carbon containing cyclic group which contains from 1 to 3 heteroatoms selected from oxygen, nitrogen and sulfur, such as morpholinyl and piperidinyl. The term "($C_{3-7}$)heterocycloalkyl($C_{1-6}$)alkyl" means a ($C_{1-6}$)alkyl group substituted by a ($C_{3-7}$)heterocycloalkyl group, for example, morpholinomethyl. The term "($C_{5-9}$)heteroaryl" means a cyclic or bicyclic, aromatic assemblage of conjugated carbon atoms and from 1 to 3 nitrogen, oxygen, and sulfur atoms, for example, pyridinyl, 2-quinoxalinyl, and quinolinyl. The term "($C_{5-9}$)heteroaryl($C_{1-6}$)alkyl" means ($C_{1-6}$)alkyl group substituted by a ($C_{5-9}$)heteroaryl group, such as, 3-quinolinylmethyl. The term "fused ($C_{6-10}$)aryl($C_{3-12}$)cycloalkyl" means a "($C_{3-12}$)cycloalkyl" group which has one or more sides shared with a "($C_{6-10}$)aryl," group and can, for example, include groups derived by the fusion of benzene and cyclopentane, that is 2-indanyl. The term "fused ($C_{6-10}$)aryl ($C_{3-12}$)cycloalkyl($C_{1-6}$)alkyl" means a ($C_{1-6}$)alkyl substituted by a fused ($C_{6-10}$)aryl($C_{3-12}$)cycloalkyl group. The term "fused ($C_{5-9}$)heteroaryl($C_{3-8}$)cycloalkyl" means a ($C_{5-9}$)heteroaryl group which has one or more sides shared with a ($C_{3-8}$)cycloalkyl group and can, for example, include groups derived by the fusion of cyclohexane and pyridine, that is tetrahydroquinoline. Finally the term "fused ($C_{5-9}$)heteroaryl($C_{3-8}$)cycloalkyl($C_{1-6}$)alkyl" means a ($C_{1-6}$)alkyl substituted by a fused ($C_{5-9}$)heteroaryl($C_{3-8}$)cycloalkyl group.

The compounds of formulae (I)–(IV) can form pharmaceutically acceptable salts with any non-toxic, organic or inorganic acid. Illustrative inorganic acids which form suitable salts include hydrochloric, hydrobromic, sulphuric and phosphoric acid and acid metal salts such as sodium monohydrogen orthophosphate and potassium hydrogen sulfate. Illustrative organic acids which form suitable salts include the mono, di and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxy benzoic, and sulfonic acids such as methane sulfonic acid and 2-hydroxyethane sulfonic acid.

Each α-amino acid has a characteristic "R-group", the R-group being the side chain, or residue, attached to the α-carbon atom of the α-amino acid. For example, the R-group side chain for glycine is hydrogen, for alanine it is methyl, for valine it is isopropyl. (Thus, throughout this specification, the $R_1$ moiety is the R-group for each indicated α-amino acid). For the specific R-groups or side chains of the α-amino acids reference to A. L. Lehninger's text on Biochemistry (see particularly Chapter 4) is helpful.

The natural amino acids, with the exception of glycine, contain a chiral carbon atom. Unless otherwise specifically indicated, the preferred compounds are the optically active amino acids of the L-configuration; however, applicants contemplate that the amino acids of the formulae (I)–(IV) compounds can be of either the D- or L- configurations or can be mixtures of the D- and L- isomers, including racemic mixtures. The recognized abbreviations for the α-amino acids are set forth in Table I.

TABLE I

| AMINO ACID | SYMBOL |
| --- | --- |
| Alanine | Ala |
| Isoleucine | Ile |
| Leucine | Leu |
| Lysine | Lys |
| Proline | Pro |
| Valine | Val |
| Norvaline | Nva |
| Norleucine | Nle |
| 1-Naphthylalanine | Nal(1) |
| 2-Indolinecarboxylic acid | Ind |
| beta-Alanine | bAla |
| beta-Valine | bVal |
| Methionine | Met |
| Ornithine | Orn |

Furthermore, the recognized abbreviations for the α-amino acids denoted by the structures and names given below are as follows:

Tic

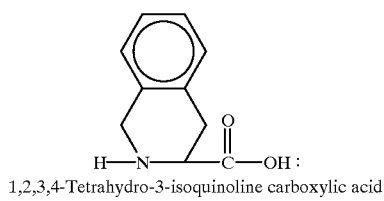
1,2,3,4-Tetrahydro-3-isoquinoline carboxylic acid

Tca

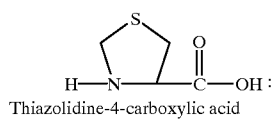
Thiazolidine-4-carboxylic acid

Aze

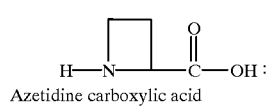
Azetidine carboxylic acid

Pip

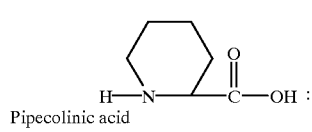
Pipecolinic acid

Pro(4-OH)

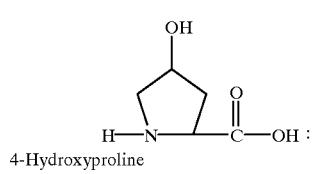
4-Hydroxyproline

Pro(4-OAc)

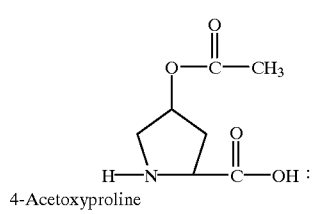
4-Acetoxyproline

Pro(4-OBzl)

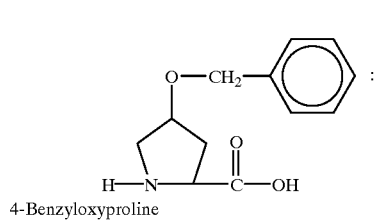
4-Benzyloxyproline

As with any group of structurally related compounds which possesses a particular generic utility, certain groups and configurations are preferred. Preferred compounds of formula (I), include the following groupings.

With respect to the substituent $P_4$, compounds of formula (I) wherein $P_4$ is Ala or a bond, are preferred. Compounds of formula (I) wherein $P_4$ is a bond are particularly preferred.

With respect to the substituent $P_3$, compounds of formula (I) wherein $P_3$ is Ile, Val or Ala, are preferred. Compounds of formula (I) wherein $P_3$ is Val are particularly preferred.

With respect to the substituent $P_2$, compounds of formula (I) wherein $P_2$ is Pro, Tic, Pip, Tca, Pro(4-OBzl), Aze, Pro(4-OAc) or Pro(4-OH) are preferred. Compounds of formula (I) wherein $P_2$ is Pro are particularly preferred.

As for substituent $R_1$, compounds of formula (I) wherein $R_1$ is $-CH(CH_3)_2$ or $-CH_2CH_2CH_3$, being the characteristic "R-groups" of the amino acids Val and Nva, respectively, are preferred. Compounds of formula (I) wherein $R_1$ is $-CH(CH_3)_2$ are particularly preferred.

With regard to the substituent K, compounds of formula (I) wherein K is benzoyl, t-butyloxycarbonyl, carbobenzyloxy, isovaleryl, $-C(=O)N(CH_3)_2$,

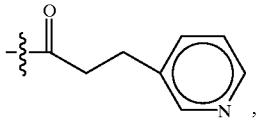

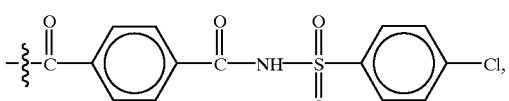

or 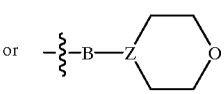

wherein
Z is N and B is a group of the formulae

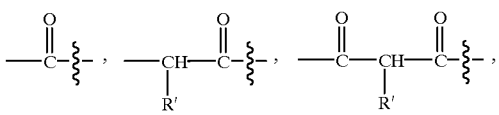

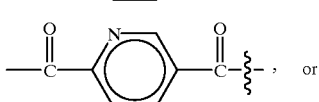 or

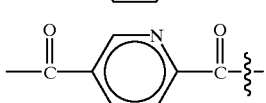

and wherein R' is hydrogen or a $(C_{1-6})$alkyl group are preferred. Compounds of formula I wherein K is

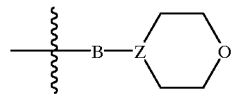

and wherein
Z is N and B is a group of the formulae

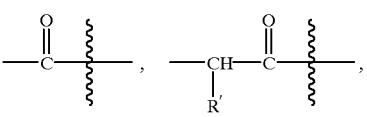

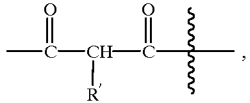

-continued

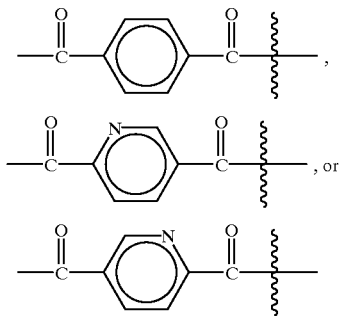

and wherein R' is hydrogen or a $C_{1-6}$ alkyl group are particularly preferred.

Specific examples of preferred compounds of formula (I) include:

N-[4-(4-morpholinylcarbonyl)benzoyl]-L-valyl-N'-[3,4,4,5,5,5-heptafluoro-1(1-methylethyl)-2-oxopentyl]-L-prolinamide N-[4-(4-morpholinylcarbonyl)benzoyl]-L-valyl-N'-[3,3,4,4,5,5,6,6,6-nonafluoro-1-(1-methylethyl)-2-oxohexyl]-L-prolinamide;

N-[(1,1-dimethylethoxy)carbonyl]-L-valyl-N'-[3,3,4,4,5,5,5-heptafluoro-1-(1-methylethyl)-2-oxopentyl]-L-prolinamide;

N-[(1,1-dimethylethoxy)carbonyl]-L-valyl-N'-[3,3,4,4,5,5,6,6,6-nonafluoro-1-(1-methylethyl)-2-oxohexyl]-L-prolinamide;

N-[4-(4-morpholinylcarbonyl)benzoyl]-L-valyl-N'-[3,3,4,4,5,5,5-heptafluoro-1-(1-methylethyl)-2-oxopentyl]-L-2-azetamide;

N-[4-(4-morpholinylcarbonyl)benzoyl]-L-valyl-N'-[3,3,4,4,5,5,6,6,6-nonafluoro-1-(1-methylethyl)-2-oxohexyl]-L-2-azetamide;

N-[1(1,1-dimethylethoxy)carbonyl]-L-valyl-N'-[3,3,4,4,5,5,5-heptafluoro-1-(1-methylethyl)-2-oxopentyl]-L-2-azetamide;

N-[(1,1-dimethylethoxy)carbonyl]-L-valyl-N'-[3,3,4,4,5,5.6,6,6-nonafluoro-1-(1-methylethyl)-2-oxohexyl]-L-2-azetamide;

N-[4-(4-morpholinylcarbonyl)benzoyl]-L-valyl-N'-[3,3,4,4,5,5,5-heptafluoro-1-(1-methylethyl)-2-oxopentyl]-D,L-2-pipecolinamide;

N-[4-(4-morpholinylcarbonyl)benzoyl]-L-valyl-N'-[3,3,4,4,5,5,6,6,6-nonafluoro-1-(1-methylethyl)-2-oxohexyl]-D,L-2-pipecolinamide;

N-[1(1,1-dimethylethoxy)carbonyl]-L-valyl-N'-[3,3,4,4,5,5,5-heptafluoro-1-(1-methylethyl)-2-oxopentyl]-D,L-2-pipecolinamide;

N-[(1,1-dimethylethoxy)carbonyl]-L-valyl-N'-[3,3,4,4,5,5,6,6,6-nonafluoro-1-(1-methylethyl)-2-oxohexyl]-D,L-2-pipecolinamide;

N-[4-(4-morpholinylcarbonyl)benzoyl]-L-valyl-N'-[3,3,4,4,5,5,5-heptafluoro-1-(1-methylethyl)-2-oxopentyl]-D,L-1,2,3,4-tetrahydro-3-isoquinolinamide;

N-[4-(4-morpholinylcarbonyl)benzoyl]-L-valyl-N'-[3,3,4,4,5,5,6,6,6-nonafluoro-1-(1-methylethyl)-2-oxohexyl]-D,L-1,2,3,4-tetrahydro-3-isoquinolinamide;

N-[(1,1-dimethylethoxy)carbonyl]-L-valyl-N'-[3,3,4,4,5,5,5-heptafluoro-1-(1-methylethyl)-2-oxopentyl]-D,L-1,2,3,4-tetrahydro-3-isoquinolinamide;

N-[(1,1-dimethylethoxy)carbonyl]-L-valyl-N'-[3,3,4,4,5,5,6,6,6-nonafluoro-1-(1-methylethyl)-2-oxohexyl]-D,L-1,2,3,4-tetrahydro-3-isoquinolinamide;

N-[4-(4-morpholinylcarbonyl)benzoyl]-L-valyl-N'-[3,3,4,4,5,5,5-heptafluoro-1-(1-methylethyl)-2-oxopentyl]-L-thiazolidine-4-carboxylic acid;

N-[4-(4-morpholinylcarbonyl)benzoyl]-L-valyl-N'-[3,3,4,4,5,5,6,6,6-nonafluoro-1-(1-methylethyl)-2-oxohexyl]-L-thiazolidine-4-carboxylic acid;

N-[(1,1-dimethylethoxy)carbonyl]-L-valyl-N'-[3,3,4,4,5,5,5-heptafluoro-1-(1-methylethyl)-2-oxopentyl]-L-thiazolidine-4-carboxylic acid;

N-[(1,1-dimethylethoxy)carbonyl]-L-valyl-N'-[3,3,4,4,5,5,6,6,6-nonafluoro-1-(1-methylethyl)-2-oxohexyl]-L-thiazolidine-4-carboxylic acid;

Preferred compounds of formula (II), include the following groupings.

With respect to the substituent $P_4$, compounds of formula (II) wherein $P_4$ is Ala or a bond, are preferred. Compounds of formula (II) wherein $P_4$ is a bond are particularly preferred.

With respect to the substituent $P_3$, compounds of formula (II) wherein $P_3$ is Ile, Val or Ala, are preferred. Compounds of formula (II) wherein $P_3$ is Val are particularly preferred.

Regarding substituent $P_2$, compounds of formula (II) wherein $P_2$ is Pro, Tic, Pip, Tca, Pro(4-OBzl), Aze, Pro(4-OAc) or Pro(4-OH) are preferred. Compounds of formula (II) wherein $P_2$ is Pro are particularly preferred.

As for substituent $R_1$, compounds of formula (II) wherein $R_1$ is —CH(CH$_3$)$_2$ or —CH$_2$CH$_2$CH$_3$, being the characteristic "R-groups" of the amino acids Val and Nva, respectively, are preferred. Compounds of formula (II) wherein $R_1$ is —CH(CH$_3$)$_2$ are particularly preferred.

With regard to the substituent K', compounds of formula (II) wherein K' is benzoyl, t-butyloxycarbonyl, carbobenzyloxy, isovaleryl, —C(=O)N(CH$_3$)$_2$,

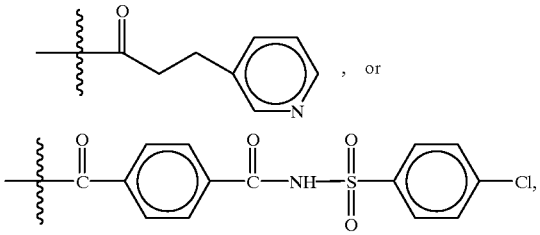

are preferred.

Specific examples of preferred compounds of formula (II) include:

N-[(1,1-dimethylethoxy)carbonyl]-L-valyl-N'-[3,3,4,4,4-pentafluro-1-(1-methylethyl)-2-oxobutyl]-L-prolinamide;

N-[(1,1-dimethylethoxy)carbonyl]-L-valyl-N-[3,3,4,4,5,5,5-heptafluoro-1-(1-methylethyl)-2-oxopentyl]-L-prolinamide;

N-[(1,1-dimethylethoxy)carbonyl]-L-valyl-N'-[3,3,4,4,5,5,6,6,6-nonafluoro-1-(1-methylethyl)-2-oxohexyl]-L-prolinamide.

Preferred compounds of formula (III), include the following groupings.

With respect to the substituent $P_4$, compounds of formula (III) wherein $P_4$ is Ala or a bond, are preferred. Compounds of formula (III) wherein $P_4$ is a bond are particularly preferred.

With respect to the substituent $P_3$, compounds of formula (III) wherein $P_3$ is Ile, Val or Ala, are preferred. Compounds of formula (III) wherein $P_3$ is Val are particularly preferred.

Regarding substituent $P_2$, compounds of formula (III) wherein $P_2$ is Pro, Tic, Pip, Tca, Pro(4-OBzl), Aze, Pro(4-OAc) or Pro(4-OH) are preferred. Compounds of formula (III) wherein $P_2$ is Pro are particularly preferred.

As for substituent $R_1$, compounds of formula (III) wherein $R_1$ is —CH(CH$_3$)$_2$ or —CH$_2$CH$_2$CH$_3$, being the characteristic "R-groups" of the amino acids Val and Nva, respectively, are preferred. Compounds of formula (III) wherein $R_1$ is —$CH(CH_3)_2$ are particularly preferred.

With regard to the substituent K", compounds of formula (III) wherein K" is

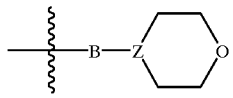

and wherein
Z is N and B is a group of the formulae

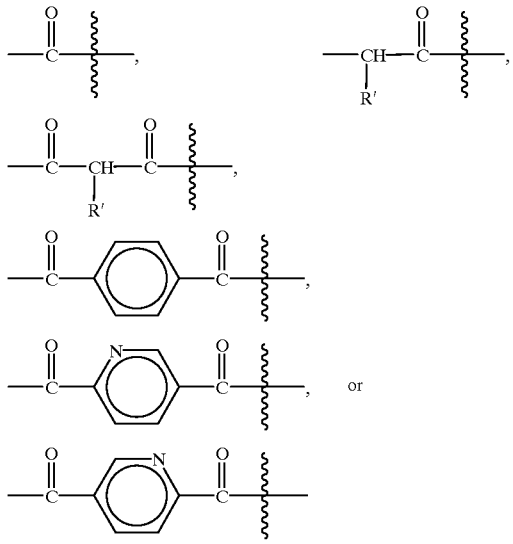

and wherein R' is hydrogen or a $C_{1-6}$ alkyl group are particularly preferred.

Specific examples of preferred compounds of formula (III) include:

N-[4-(4-morpholinylcarbonyl)benzoyl]-L-valyl-N'-[3,3,4,4,4-pentafluro-1-(1-methylethyl)-2-oxobutyl]-L-prolinamide;

N-[4-(4-morpholinylcarbonyl)benzoyl]-L-valyl-N'-[3,3,4,4,5,5,5-heptafluoro-1-(1-methylethyl)-2-oxopentyl]-L-prolinamide;

N-[4-(4-morpholinylcarbonyl)benzoyl]-L-valyl-N'-[3,3,4,4,5,5,6,6,6-nonafluoro-1-(1-methylethyl)-2-oxohexyl]-L-prolinamide.

Preferred compounds of formula (IV), include the following groupings.

With respect to the substituent $P_4$, compounds of formula (IV) wherein $P_4$ is Ala or a bond, are preferred. Compounds of formula (IV) wherein $P_4$ is a bond are particularly preferred.

With respect to the substituent $P_3$, compounds of formula (IV) wherein $P_3$ is Ile, Val or Ala, are preferred. Compounds of formula (IV) wherein $P_3$ is Val are particularly preferred.

Regarding substituent $P_2$, compounds of formula (IV) wherein $P_2$ is Pro, Ind, Tic or Tca are preferred. Compounds of formula (IV) wherein $P_2$ is Pro are particularly preferred.

With regard to the substituent $P_1$, compounds of formula (IV) wherein $P_1$ is Val or Nva are particularly preferred.

Specific examples of preferred compounds of formula (IV) include:

N-[3-(3-pyridyl)propanoyl]-L-valyl-N'-[3,3,4,4,4-pentafluro-1-(1-methylethyl)-2-oxobutyl]-L-prolinamide;

N-[3-(3-pyridyl)propanoyl]-L-valyl-N'-[3,3,4,4,4-pentafluoro-1-(1-methylethyl)-2-oxobutyl]-D,L-1,2,3,4-tetrahydro-3-isoquinolinamide;

N-[3-(3-pyridyl )propanoyl]-L-valyl-N'-[3,3,4,4,4-pentafluro-1-(1-methylethyl)-2-oxobutyl]-L-thiazolidine-4-carboxylic acid In general, the compounds of formulae (I)–(IV) may be prepared using standard chemical reactions analogously known in the art and as depicted in Scheme A.

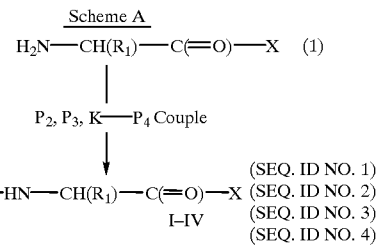

The $P_2$, $P_3$ and K—$P_4$ groups can be linked to the free amino group of the amino acid derivative of structure (1). Note that structure (1) represents the $P_1$ moiety wherein the free carboxylic acid group has be en substituted with an "X" moiety as defined above. The $P_2$, $P_3$ and K—$P_4$ can be linked to the unprotected, free amino compound ($P_1$-X) by well known peptide coupling techniques. Furthermore, the $P_1$, $P_2$, $P_3$ and K—$P_4$ groups may be linked together in any order as long as the final compound is K—$P_4$—$P_3$—$P_2$—$P_1$—X. For example, K—$P_4$ can be linked to $P_3$ to give K—$P_4$—$P_3$ which is linked to $P_2$—$P_1$—X; Or K—$P_4$ linked to $P_3$—$P_2$ then linked to an appropriately C-terminal protected $P_1$ and the C-terminal protecting group converted to X.

Generally, peptides are elongated by deprotecting the A-amine of the N-terminal residue and coupling the next suitably N-protected amino acid through a peptide linkage using the methods described. This deprotection and coupling procedure is repeated until the desired sequence is obtained. This coupling can be performed with the constituent amino acids in stepwise fashion, as depicted in Scheme A, or by condensation of fragments (two to several amino acids), or combination of both processes, or by solid phase peptide synthesis according to the method originally described by Merrifield, *J. Am. Chem. Soc.*, 1963, 85, 2149–2154, the disclosure of which is hereby incorporated by reference. When a solid phase synthetic approach is employed, the C-terminal carboxylic acid is attached to an insoluble carrier (usually polystyrene). These insoluble carriers contain a group which will react with the aldehyde group to form a bond which is stable to the elongation conditions but readily cleaved later. Examples of which are: chloro- or bromomethyl resin, hydroxymethyl resin, and aminomethyl resin. Many of these resins are commercially available with the desired C-terminal amino acid already incorporated.

Alternatively, compounds of the invention can be synthesized using automated peptide synthesizing equipment. In addition to the foregoing, peptide synthesis are described in Stewart and Young, "Solid Phase Peptide Synthesis", 2nd ed., Pierce Chemical Co., Rockford, Ill. (1984); Gross, Meienhofer, Udenfriend, Eds., "The Peptides: Analysis, Synthesis, Biology", Vol 1, 2, 3, 5 and 9, Academic Press, New York, 1980–1987; Bodanszky, "Peptide Chemistry: A Practical Textbook", Springer-Verlag, New York (1988): and BodanszKy, et al. "The Practice of Peptide Synthesis" Springer-Verlag, New York (1984), the disclosures of which are hereby incorporated by reference.

Coupling between two amino acids, an amino acid and a peptide, or two peptide fragments can be carried out using standard coupling procedures such as the azide method, mixed carbonic-carboxylic acid anhydride (isobutyl chloroformate) method, carbodiimide (dicyclohexylcarbodiimide, diisopropylcarbodiimide, or water-soluble carbodiimide) method, active ester (p-nitrophenyl ester, N-hydroxy-succinic imido ester) method, Woodward reagent K method, carbonyldiimidazole method, phosphorus reagents such as BOP—Cl, or oxidation-reduction methods. Some of these methods (especially the carbodiimide method) can be enhanced by adding 1-hydroxybenzotriazole, N-hydroxysuccinimide, dimethylamino pyridine or the like. These coupling reactions can be performed in either solution (liquid phase) or solid phase.

The functional groups of the constituent amino acids generally must be protected during the coupling reactions to avoid formation of undesired bonds. The protecting groups that can be used are listed in Greene, "Protective Groups in Organic Chemistry", John Wiley & Sons, New York (1981) and "The Peptides: Analysis, Synthesis, Biology", Vol. 3, Academic Press, New York (1981), the disclosure of which is hereby incorporated by reference.

The α-carboxyl group of the C-terminal residue is usually, but does not have to be, protected by an ester that can be cleaved to give the carboxylic acid. Protecting groups which can be used include: 1) alkyl esters such as methyl and t-butyl, 2) aryl esters such as benzyl and substituted benzyl, or 3) esters which can be cleaved by mild base treatment or mild reductive means such as trichloroethyl and phenacyl esters.

The α-amino croup of each amino acid to be coupled to the growing peptide chain must be protected. Any protecting group known in the art can be used. Examples of which include: 1) acyl types such as formyl, trifluoroacetyl, phthalyl, and p-toluenesulfonyl; 2) aromatic carbamate types such as benzyloxycarbonyl (Cbz or Z) and substituted benzyloxycarbonxyls, 1-(p-biphenyl)-1-methylethoxycarbonyl, and 9-fluorenylmethyloxycarbonyl (Fmoc); 3) aliphatic carbamate types such as tertbutyloxycarbonyl (Boc), ethoxycarbonyl, diisopropylmethoxycarbonyl , and allyloxycarbonyl; 4) cyclic alkyl carbamate types such as cyclopentyloxycarbonyl and adamantyloxycaronbyl; 5) alkyl types such as triphenylmethyl and benzyl; 6) trialkylsilane such as trimethylsilane, and 7) thiol containing types such as phenylthiocarbonyl and dithiasuccinoyl. The preferred α-amino protecting group is either Boc or Fmoc, preferably Boc. Many amino acid derivaties suitably protected for peptide synthesis are commercially available.

The α-amino group protecting group of the newly added amino acid residue is cleaved prior to the coupling of the next amino acid. When the Boc group is used, the methods of choice are trifluoroacetic acid, neat or in dichloromethane, or HCl in dioxane diethyl ether, or ethyl acetate. The resulting ammonium salt is then neutralized either prior to the coupling or in situ with basic solutions such as aqueous buffers, or tertiary amines in dichloromethane or dimethlformamide. When the Fmoc group is used, the reagents of choice are piperidine or substituted piperidine in dimethylformamide, but any secondary amine or aqueous basic solutions can be used. The deprotection is carried out at a temperature between 0° C. and room temperature.

Any of the amino acids bearing side chain functionalities must be protected during the preparation of the peptide using any of the above-described groups. Those skilled in the art will appreciate that the selection and use of appropriate protecting groups for these side chain functionalities depends upon the amino acid and presence of other protecting groups in the peptide. The selection of such protecting groups is important in that it must not be removed during the deprotection and coupling of the α-amino group.

For example, when Boc is used as the α-amino protecting group, the following side chain protecting groups are suitable: p-toluenesulfonyl (tosyl) moieties can be used to protect the amino side chains of amino acids such as Lys and Arg; p-methylbenzyl, acetamidomethyl, benzyl (Bzl), or t-butylsulfonyl moieties can be used to protect the sulfide containing side chains of amino acids such as cysteine and benzyl (Bzl) ether can be used to protect the hydroxy containing side chains of amino acids such as Ser or Thr.

When Fmoc is chosen for the α-amine protection, usually tert-butyl based protecting groups are acceptable. For instance, Boc can be used for lysine, tert-butyl ether for serine and threonine and tert-butyl ester for glutamic acid.

Once the elongation of the peptide is completed all of the protecting groups are removed. When a liquid phase synthesis is used, the protecting groups are removed in whatever manner is dictated by the choice of protecting groups. These procedures are well known to those skilled in the art.

When a solid phase synthesis is used, the peptide is cleaved from the resin usually simultaneously with the protecting group removal. When the Boc protection scheme is used in the synthesis, treatment with anhydrous HF containing additivies such as dimethyl sulfide, anisole, thioanisole, or p-cresol at 0° C. is the preferred method for cleaving the peptide from the resin. The cleavage of the peptide can also be accomplished by other acid reagents such as trifluoromethanesulfonic acid/trifluoroacetic acid mixtures. If the Fmoc protection scheme is used the N-terminal Fmoc group is cleaved with reagents described earlier. The other protecting groups and the peptide are cleaved from the resin using solution of trifluoroacetic acid and various additives such as anisole, etc.

Alternatively, the compounds of formulae (I)–(IV) may be prepared using standard chemical reactions analogously known in the art and as depicted in Scheme B.

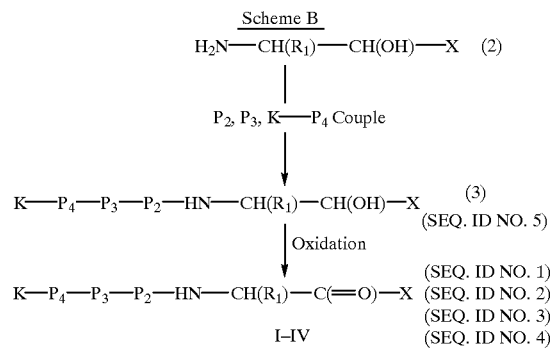

Scheme B provides an alternative general synthetic scheme for preparing the compounds of formulae (I)–(IV).

The $P_2$, $P_3$ and K—$P_4$ groups can be linked to the free amino group of the amino alcohol derivative of structure (2) as described previously in Scheme A to give the peptido alcohol of structure (3).

The alcohol functionality of the peptido alcohol of structure (3) is then oxidized-by techniques and procedures well known and appreciated by one of ordinary skill in the art, such as a Swern Oxidation using oxalyl chloride or trifluoroacetic anhydride and dimethylsulfoxide, to give the compounds of formula I.

Starting materials for use in Schemes A and B are readily available to one of ordinary skill in the art. For example, amino acids $P_2$, $P_3$ and K—$P_4$ wherein K is hydrogen are commercially available and the linker compound of structure (L1) is described in *J. Am. Chem. Soc.,* 114, 3157–59 (1992). In addition, substituted amino acids K—$P_4$ wherein (is acetyl, succinyl, benzoyl, t-butyloxycarbonyl, carbobenzyloxy, tosyl, dansyl, isovaleryl, methoxysuccinyl, 1-adamantanesulphonyl, 1-adamantaneacetyl, 2-carboxybenzoyl, phenylacetyl, t-butylacetyl, bis [(1-naphthyl)-methyl)acetyl or —A—$R_z$ wherein

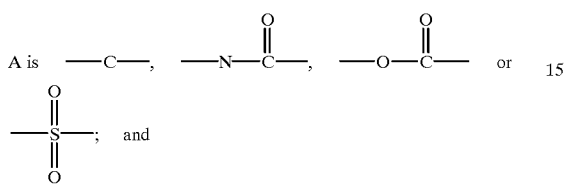

$R_z$ is an aryl group containing 6, 10 or 12 carbons suitably, suitably substituted by 1 to 3 members selected independently from the group consisting of fluoro, chloro, bromo, iodo, trifluoromethyl, hydroxy, alkyl containing from 1 to 6 carbons, alkoxy containing from 1 to 6 carbons, carboxy, alkylcarbonylamino wherein the alkyl group contains 1 to 6 carbons, 5-tetrazolyl, and acylsulfonamido (i.e., acylaminosulfonyl and sulfonylaminocarbonyl) containing from 1 to 15 carbons, provided that when the acylsulfonamido contains an aryl the aryl may be further substituted by a member selected from fluoro, chloro, bromo, iodo and nitro; and such other terminal amino protecting groups which are functionally equivalent thereto are described in European Patent Application OPI No. 0363284, Apr. 11, 1990.

Starting amino compounds of structure (1) are readily available to one of ordinary skill in the art. For example, amino compounds of structure (1) wherein X is —$CF_2CF_3$ are described in European Patent Application OPI No. 0503203, Sep. 16, 1992. In addition, amino compounds of structure (1) wherein X is —$CF_2CF_3$ are described in European Patent Application OPI No. 0410411, January 30, 1991.

In addition, other starting materials for use in Schemes A and B may be prepared by the following synthetic procedures which are well known and appreciated by one of ordinary skill in the art.

Substituted amino acids K—$P_4$ of structure wherein K is

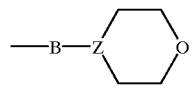

wherein
Z is N or CH, and
B is a group of the formulae

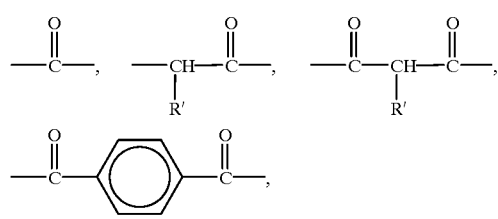

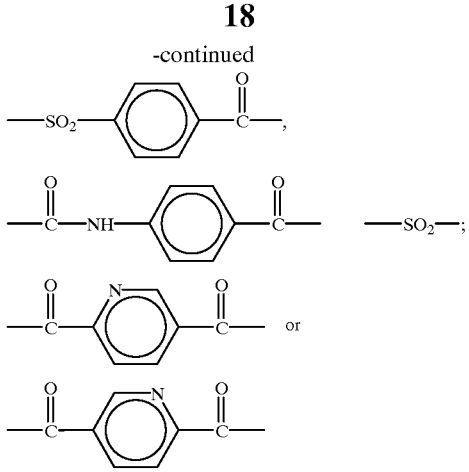

wherein R' is hydrogen or a $C_{1-6}$ alkyl group are prepared using standard chemical reactions analogously known in the art.

The procedure for preparing the substituted amino acids K—$P_4$ wherein K is

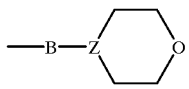

wherein
B is a —C(=O)— is outlined in Scheme C wherein $P_4$ and Z are as previously defined or are the functional equivalents of these groups.

Scheme C

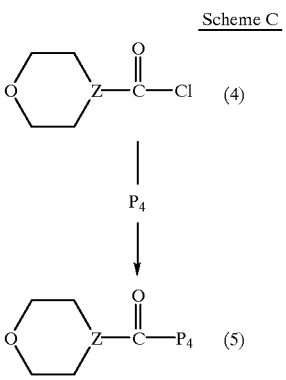

Specifically the amino acids K—$P_4$ wherein K is

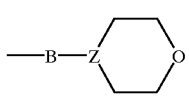

wherein
B is a —C(=O)— are prepared by coupling of the amino acid K—$P_4$ wherein K is hydrogen with an acid chloride of structure (4) in the presence of from one to four molar equivalents of a suitable amine which can act as a hydrogen halide acceptor. Suitable amines for use as hydrogen halide acceptors are tertiary organic amines such as tri-(lower alkyl)amines, for example, triethylamine, or aromatic amines such as picolines, collidines, and pyridine. When pyridines, picolines, or collidines are employed, they can be used in high excess and act therefore also as the reaction solvent. Particularly suitable for the reaction is N-methylmorpholine ("NMM"). The coupling reaction can be performed by adding an excess, such as from 1–5, preferably about a 4-fold molar excess of the amine and then the acid chloride of structure (4), to a solution of the amino acid K—$P_4$ wherein K is hydrogen. The solvent can be any suitable solvent, for example, petroleum ethers. a chlorinated hydrocarbon such as carbon tetrachloride, ethylene chloride, methylene chloride, or chloroform; a chlorinated aromatic such as 1,2,4-trichlorobenzene, or o-dichlorobenzene; carbon disulfide; an ethereal solvent such as diethylether, tetrahydrofuran, or 1,4-dioxane, or an aromatic solvent such as benzene, toluene, or xylene. Methylene chloride is the preferred solvent for this coupling reaction. The reaction is allowed to proceed for from about 15 minutes to about 6 hours, depending on the reactants, the solvent, the concentrations, and other factors, such as the temperature which can be from about 0° C. to about 60° C., conveniently at about room temperature, i.e. 25° C. The N-protected amino acids K—$P_4$ wherein K is

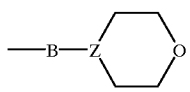

wherein
B is a —C(=O)— can be isolated from the reaction mixture by any appropriate techniques such as by chromatography on silica gel.

The substituted amino acids K—$P_4$ wherein K is

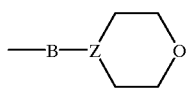

wherein
B is other than a —C(=O)— can be prepared analogously, merely by substituting the appropriate intermediate

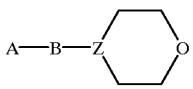

wherein
B is other than a —C(=O)— and A is Cl or OH (the corresponding acid, acid chloride or sulphonyl chloride) for the compound of structure (5) in Scheme C.

The acid chloride of structure (4) and the appropriate intermediate of formula

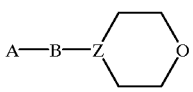

wherein
B is other than a —C(=O)— and A is Cl or OH (the corresponding acid, acid chloride or sulphonyl chloride) are commercially available or may be readily prepared by techniques and procedures well known and appreciated by one of ordinary skill in the art.

For example, the appropriate intermediates of formula

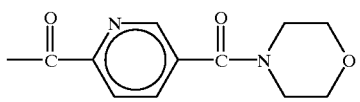

may be prepared as outlined in Scheme D wherein all substituents are as previously defined.

Scheme D

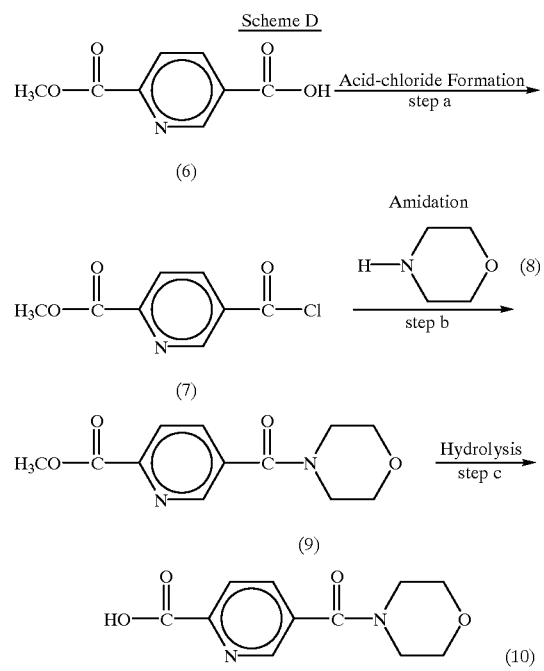

Scheme D provides a general synthetic procedure for preparing the appropriate intermediates of formula

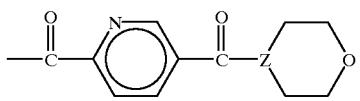

wherein
Z is as previously defined.

In step a, the carboxylic acid functionality of the appropriate 2,5-pyridinedicarboxylic acid, 2-methyl ester (6) (*Nippon Kagaku Zasshi*, 1967, 88, 563) is converted to its acid chloride using techniques and procedures well known and appreciated by one of ordinary skill in the art, such as thionyl chloride, to give the corresponding 6-carbomethoxynicotinoyl chloride (7).

In step b, the acid chloride (7) is amidated with morpholine (8) by techniques and procedures well known and appreciated by one of ordinary skill in the art to give the corresponding 5-(morpholine-4-carbonyl)-2-pyridinecarboxylic acid, methyl ester (9).

In step c, the methyl ester functionality (9) is hydrolyzed by techniques and procedures well known and appreciated by one of ordinary skill in the art, with for example, lithium hydroxide in methanol, to give 5-(morpholine-4-carbonyl)-2-pyridine carboxylic acid (10).

In addition, the appropriate intermediate of formula

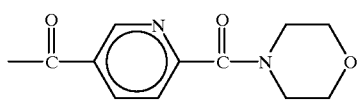

may be prepared as outlined in Scheme E wherein all substituents are as previously defined.

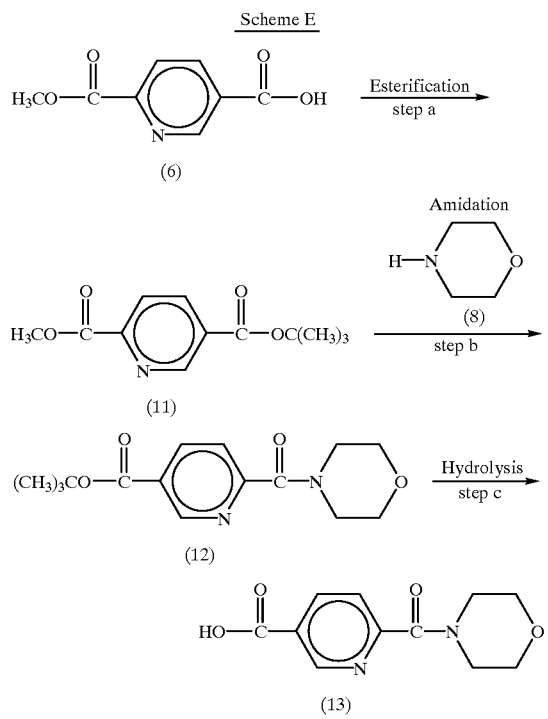

Scheme E provides a general synthetic procedure for preparing the appropriate intermediates of formula

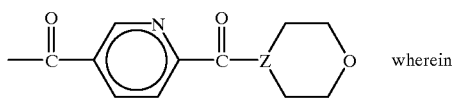 wherein

Z is as previously defined.

In step a, the free carboxylic acid functionality of 2,5-pyridinedicarboxylic acid, 2-methyl ester (6) (*Nippon Kagaku Zasshi,* 1967, 88, 563) is converted to its t-butyl ester using techniques and procedures well known and appreciated by one of ordinary skill in the art, such as the t-butyl alcohol adduct of dicyclohexylcarbodiimide (*Synthesis,* 1979, 570), to give the corresponding 2,5-pyridinedicarboxylic acid, 2-methyl ester, 5-t-butyl ester (11).

For example, the 2,5-pyridinedicarboxylic acid, 2-methyl ester (6) is combined with a molar excess of the t-butyl alcohol adduct of dicyclohexylcarbodiimide in an appropriate organic solvent, such as methylene chloride. The reaction is typically conducted at a temperature range of from 0° C. room, temperature and for a period of time ranging from 2–24 hours. The 2,5-pyridinedicarboxylic acid, 2-methyl ester, 5-t-butyl ester (11) is isolated from the reaction mixture by standard extractive methods as is known in the art and may be purified by crystallization.

In Step b, the methyl ester functionality of (11) is amidated with morpholine (8) to give the corresponding 6-(morpholine-4-carbonyl)nicotinic acid, t-butyl ester (12).

For example, the 2,5-pyridinedicarboxylic acid, 2-methyl ester, 5-t-butyl ester (11) is contacted with a molar excess of morpholine in an appropriate organic solvent, such as tetrahydrofuran. The reaction is typically conducted at a temperature range of from room temperature to reflux and for a period of time ranging from 5 hours to 3 days. The 6-(morpholine-4-carbonyl)nicotinic acid, t-butyl ester (12) is isolated from the reaction mixture by standard extractive methods as is known in the art and may be purified by crystallization.

In step c, the t-butyl ester functionality of (12) is hydrolyzed, with for example, HCl in nitromethane, to give the corresponding, 6-(morpholine-4-carbonyl)nicotinic acid (13).

Alternate routes for the preparation of compounds of structure (1) wherein X=—CF$_2$CF$_3$, is shown in scheme F.

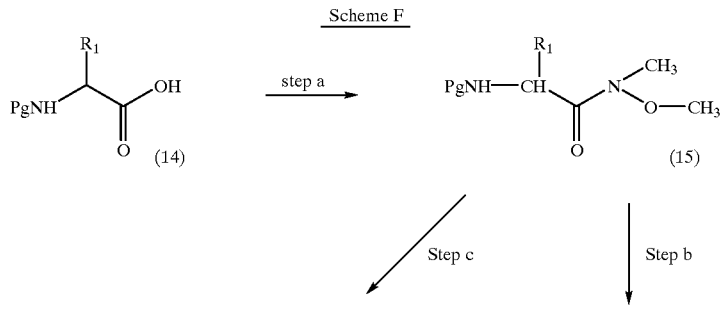

-continued

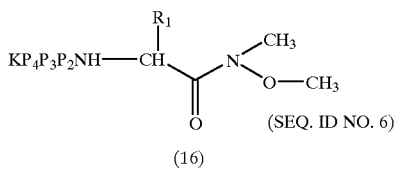
(SEQ. ID NO. 6)
(16)

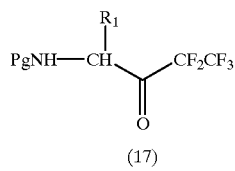
(17)

Step b

Step d

KP$_4$P$_3$P$_2$NH—CH(R$_1$)—C(O)—CF$_2$CF$_3$
(SEQ. ID NO. 7)
(18)

The required starting material defined by compound (14) is readily available either commercially or by applying known prior art principles and techniques. The term "Pg" refers to a suitable protecting group as more fully defined previously.

In Scheme F, step a the protected amino acid (14) is transformed into the hydroxamate (15). This amidation can be performed utilizing a coupling reaction as between two amino acids using the protected amino acid (14) and the N-alkyl O-alkylhydroxylamine. The standard coupling reaction can be carried out using standard coupling procedures as described previously for the coupling between two amino acids to provide the hydroxamate (15).

In step b, the protected hydroxamate (15) ip transformed into the protected pentafluoroketone (17) for (18)]. This reaction can be performed utilizing a reaction of the type described in the following reference M. R. Angelastro, J. P Burkhart, P. Bey, N. P. Peet, *Tetrahedron Letters*, 33 (1992), 3265–3268.

In step c, the hydroxamate (15) is deprotected under conditions well known in the art as described by T. H. Green "Protection Groups in Organic Synthesis", John Wiley and Sons, 1981, Chapter 7, to provide the deprotected hydroxamate. The deprotected hydroxamate is elongated by coupling the next suitably protected amino acid through a peptide linkage using the methods previously described in Scheme A, or by condensation of fragments, or combination of both processes to provide the elongated peptide (16).

In step d, the ketone (17) is deprotected under conditions as previously described. The deprotected ketone (17) is elongated by coupling the next suitably protected amino acid through a peptide linkage using the methods previously described in Scheme A, or by condensation of fragments, or combination of both processes to provide the elongated ketone (18).

Alternatively, the corresponding N-protected amino acid ester of (14) [i.e. PgNH—CH(R$_1$)C(=O)OR$_2$, (15a), wherein R$_2$ and Pg are as defined above] can be substituted for the hydroxamate (15). The corresponding protected amino acid esters of (14) are commercially available or easily synthesized from (14) by procedures well known by one of ordinary skill in the art. In step b, the amino acid ester (15a), is transformed into the N-protected pentafluoroketone (17) [or (18)] in a manner directly analogous to that used for the corresponding hydroxamate. Steps c and d would be the same as those employed when utilizing the hydroxamate (15).

Scheme F is also applicable for the preparation of compounds of structure (1) wherein X is —CF$_2$CF$_2$CF$_3$ or —CF$_2$CF$_2$CF$_2$CF$_3$, the amino acid ester (15a) being reacted with a suitable perfluorinating agent, such as, from 4–8 equivalents of perfluoropropyl iodide or perfluorobutyl iodide, although the equivalent bromides may also be used. Said reaction is carried out in the presence of a suitable alkali metal base, for example from 4–8 equivalents of MeLi/LiBr in an appropriate anhydrous solvent (or mixed solvents), such as ether, t-butylmethyl ether or toluene. Other examples of suitable alkali metal bases include t-BuLi, EtMgBr, PhMgBr, n-BuLi, and the like. The reaction is carried out at reduced temperature of from –100° C. to 0° C., preferably from –30° C. to –80° C., to provide the protected perfluoropropyl amino ketone and the protected perfluorobutyl amino ketone, respectively. Steps c and d would be the same as those employed when utilizing the hydroxamate (15).

Alternatively, the N-protected amino acid ester (15a) could first be deprotected and coupled with a suitably N-protected peptide in the presence of a suitable coupling agent and in the presence of an appropriate coupling solvent. The subsequently formed N-protected peptide ester [KP$_4$P$_3$P$_2$NH—CH(R$_1$)C(=O)OR$_2$, (16a)] would then be perfluorinated in a manner directly analogous to that used for the corresponding hydroxamate. Steps c and d would be the same as those employed when utilizing the hydroxamate (16).

For the purposes of this invention, the terms "suitable coupling agent" and "appropriate coupling solvent" are meant to include any of the standard coupling reagents and solvents used in the standard coupling procedures defined above. Similarly, the terms "suitable deprotecting agent" and "appropriate organic solvent" are intended to include any of the standard deprotecting agents and solvents used in the standard deprotection procedures described above. Related procedures are described in Gassman, P. G., O'Reilly, N. J., *J. Org. Chem.* 1987, 52, 2481 and Portella, C., Doussot, P., Dondy, B., *Synthesis* 1992, 995.

All of the amino acids employed in the synthesis of Formula 1 are either commercially available or are easily synthesized by one skilled in the pertinent art. For example, the amino acid derivative

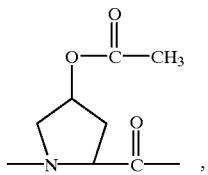

defined in P₂ can be made by esterifying

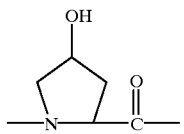

by utilizing techniques well-known by one of ordinary skill in the art.

The following examples present typical syntheses as described in Scheme A through F. These examples are understood to be illustrative only and are not intended to limit the scope of the present invention in any way. As used herein, the following terms have the indicated meanings: "g" refers to grams; "mmol" refers to millimoles; "mL" refers to milliliters; "bp" refers to boiling point; "° C." refers to degrees Celsius; "mm Hg" refers to millimeters of mercury; "μL" refers to microliters; "μg" refers to micrograms; and "μM" refers to micromolar; "DME" refers to 1,2-dimethoxyethane; "DCC" refers to dicyclohexylcarbodiimide; "h" refers to hour; "DMF" refers to N,N'-dimethylformamide; "conc" refers to concentrated; "NMM" refers to N-methylmorpholine, "in vacuo" refers to removal of solvent under reduced pressure; "GC" refers to gas chromatography; "$R_t$" refers to retention time.

EXAMPLE 1

Preparation of N-[(1,1-dimethylethoxy)carbonyl]-L-valyl-N'-[3-methoxy-1-(1-methylethyl)-2-oxopropyl]-L-prolinamide

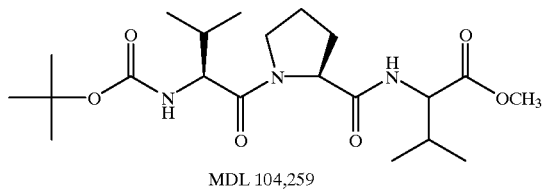

MDL 104,259

To a solution of N-(tert-butyloxycarbonyl)-L-valyl-L-proline (from Advanced ChemTech, 3.1 g, 0.01 mol) and NMM (1.10 mL, 0.01 mol) in CH₂Cl₂ (100 mL) at −20° C. was added isobutylchloroformate (1.30 mL, 0.01 mol) at −20° C. After stirring for 20 min, an additional equivalent of NMM (1.10 mL, 0.01 mol) was added followed by the addition of L-valine methyl ester hydrochloride (1.67 g, 0.01 mol, Aldrich) as a solid in one portion. The reaction was stirred at −20° C. for an additional 1 h and then allowed to warm to room temperature. The reaction mixture was then diluted with an additional CH₂Cl₂ (50 mL) and washed with 1N HCl (3×50 mL), saturated NaHCO₃ (2×50 mL) and brine (1×50 mL). The resulting organic extract was dried (MgSO₄) and concentrated in vacuo to give the desired product (MDL 104,259) (4.27 g, 100%) as a white foam. TLC $R_f$ 0.33 (3:1 Et₂O-hexane): FT-IR (KBr) 3553, 3537, 3520, 3510, 3310, 2968, 2935, 2876, 1741, 1687, 1631, 1527, 1440, 1390, 1367, 1338, 1309, 1244, 1203, 1172, 1114, 1093, 1043, 1016, 962, 923, 883, 831, 754, 665, 628, 603 cm⁻¹; ¹H NMR (300 MHz, CDCl₃)δ 7.22 (br d, 1H, J=8.4 Hz, NH), 5.24 (br d, 1H, J=11.0 Hz, NH), 4.62 (dd, 1H, J=8.2, 2.9 Hz, CH of Val), 4.43 (app. dd, 1H, J=8.6, 5.1 Hz, CH of Pro), 4.30 (dd, 1H, J=9.5, 6.4 Hz, CH of Val), 3.75–3.70 and 3.63–3.59 (pr m, 2H, CH₂N), 3.7 (s, 3H, OMe), 2.36 (m, 1H, β-CH of Val), 2.17–1.91 (m, 5H, CH₂CH₂ and β-CH of Val), 1.43 (s, 9H, t-Bu), 1.00 (d, 3H, J=6.7 Hz, CH₃), 0.95–0.90 (m, 9H, 3×CH₃); ¹³C CMRδ 172.5, 172.1, 170.9, 155.8, 79.5, 77.4, 77.1, 76.9, 76.8, 76.5, 59.9, 57.5, 56.7, 52.0, 47.6, 31.4, 31.0, 28.3, 28.2, 27.1, 25.1, 19.5, 18.9, 17.8, 17.3; MS (CI/CH₄) m/z (rel intensity) 428 (MH⁺, 22), 372 (68), 328 (100). Anal. Calcd. for C₂₁H₃₇N₃O₆: C, 58.99; H, 8.72; N, 9.83. Found: C, 58.68; H, 8.79; N, 9.55.

EXAMPLE 2

Preparation of N-[1,1-dimethylethoxy)carbonyl]-L-valyl-N'-[3,3,4,4,4-pentafluoro-1-(1-methylethyl)-2-oxopropyl]-L-prolinamide

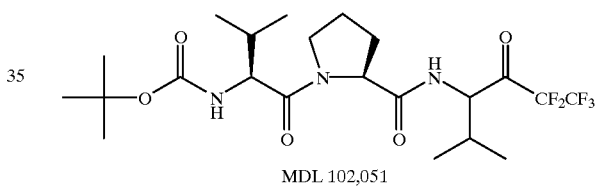

MDL 102,051

To a −78° C. solution of the product of example 1 (3.8 g, 9.0 mmol) in Et₂O (100 mL) was added condensed pentafluroethyl iodide (5.5 mL, 48.0=ol). To the mixture methyllithium-lithium bromide complex (28.5 mL, 42.0 mmol) was added at a rate which maintained an internal reaction temperature below −70° C. The reaction mixture was stirred at −78° C. for 0.5 h, the cold bath removed and stirring continued 5 min. The mixture was poured into H₂O (100 mL) and the aqueous phase was acidified with 1 N HCl. The aqueous phase was extracted with additional Et₂O (100 mL) and the combined ethereal extracts dried (MgSO₄). The solvent was removed in vacuo to yield a crude yellow oil which was immediately flash chromatographed (4.0×25 cm column eluted with 3:1 Et₂O-hexane) to give the desired product (MDL 102,051) (1.95 g, 42%) as a white foam; ¹H NMR (300 MHz, CDCl₃)δ 7.60 (br d, 1H, J=7.6 Hz, NH), 5.23 (br d, 1H, 7.9.2 Hz, NH), 4.94 (dd, 1H, J=7.6, 4.4 Hz, C₃ of Val), 4.63 (dd, 1H, 58.1, 2.8 Hz, CH of Pro), 4.28 (dd, 1H, J=9.3, 6.5 Hz, α-CH of Val), 3.81–3.69 and 3.64–3.54 (pr m, 2H, CH₂N), 2.44–1.81 (series of m, 6H, β-CH of Val, CH₂CH₂), 1.44 (s, 9H, t-Bu), 1.02 (d, 3H, J=6.8 Hz, CH₃), 0.98 (d, 3H, J=6.8 Hz, CH₃), 0.95 (d, 3H, J=6.8 Hz, CH₃), 0.88 (d, 3H, J=6.8 Hz, CH₃); ¹⁹F NMRδ −82.15 (s, CF₃), −121.70 and −122.70 (AB quartet, J=296 Hz, CF₂); MS (CI/CH₄) m/z (rel. intensity) 516 (MH⁺, 52), 460 (100), 416 (26).

EXAMPLE 3

Preparation of N-[(1,1-dimethylethoxy)carbonyl]-L-valyl-N'-[3,3,4,4,5,5,5-heptafluoro-1-(1-methylethyl)-2-oxopentyl]-L-prolinamide

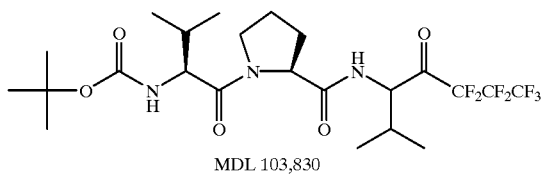

MDL 103,830

To a −78° C. solution of the product of example 1 (3.8 g, 9.0 mmol) in Et$_2$O (100 mL) was added, dropwise, under N$_2$, perfluoropropyl iodide (6.6 mL, 48.0 mmol, from Aldrich, stabilized with Cu). To this mixture methyllithium-lithium bromide complex (28.5 mL, 42.0 mmol) was added at a rate which maintained an internal reaction temperature below −70° C. The reaction mixture was stirred at −78° C. for 1 h, the cold bath removed and stirring continued 5 min. The mixture was poured into H$_2$O (100 mL) and the aqueous phase was acidified with 1 N HCl. The aqueous phase was extracted with addition, Et$_2$O (100 mL) and the combined ethereal extracts dried (MgSO$_4$). The solvent was removed in vacuo to yield a crude yellow oil which was immediately flash chromatographed (4.0×25 cm column eluted with 3:1 Et$_2$O-hexane) to give the desired product (MDL 103,830) (654 mg, 13%) as a white foam; FT-IR (KBr) 3423, 3292, 2972, 2937, 2879, 2823, 2771, 2739, 2253, 1755, 1687, 1635, 1525, 1444, 1392, 1367, 1348, 1313, 1232, 1178, 1126, 1041, 1018, 966, 922, 910, 877, 837, 798, 756, 736, 667, 650, 632, 596 cm$^{-1}$; $^1$H NMR (300 MHz, CDCl$_3$)δ 7.63 (d, 1H, J=8.2 Hz, NH), 5.44 (d, 1H, J=9.2 Hz, NH), 5.02 (dd, 1H, J=7.8, 4.5 Hz, CH of Val), 4.64 (dd, 1H, J=8.0, 3.0 Hz, CH of Pro), 4.30 (dd, 1H, J=9.2, 6.8 Hz, α-CH of Val), 3.80–3.74 and 3.66–3.60 (pr m, 2H, CH$_2$N), 2.31–1.92 (series of m, 6H, β-CH of Val, CH$_2$CH$_2$), 1.44 (s, 9H, t-Bu), 1.02 (d, 3H, J=7.0 Hz, CH$_3$), 0.98 (d, 3H, J=6.9 Hz, CH$_3$), 0.94 (d, 3H, J=6.7 Hz, CH$_3$), 0.88 (d, 3H, J=6.9 Hz, CH$_3$); $^{13}$C NMRδ 193.3, 193.0, 192.7, 172.9, 171.1, 155.7, 118.7, 115.8, 111.3, 108.9, 108.6, 108.2, 105.9, 79.6, 77.3, 77.2, 76.9, 76.6, 59.7, 59.3, 56.8, 47.8, 31.4, 29.0, 29.3, 26.9, 25.1, 19.9, 19.8, 19.7, 19.5, 19.4, 17.5, 17.4, 16.3, 16.1; $^{19}$F NMR (376.3 MHz, CDCl$_3$)δ −80.91 (t, CF$_3$), −119.03 and −120.43 (AB quartet, J=297 Hz, CF$_2$), −126.62 (s, CF$_2$): MS (CI/CH$_4$) m/z (rel. intensity) 566 (MH$^+$, 100). HRMS (C$_{23}$H$_{34}$F$_7$N$_3$O$_5$) (M$^+$) calcd 566.2492, obsd 566.2475.

EXAMPLE 4

Preparation of N-[(1,1-dimethylethoxy)carbonyl]-L-valyl-N'-[3,3,4,4,5,5,6,6,6-nonafluoro-1-(1-methylethyl)-2-oxohexyl]-L-prolinamide

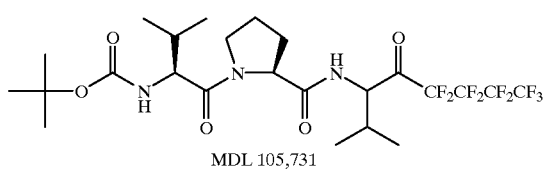

MDL 105,731

To a −78° C. solution of the product of example 1 (3.89, 9.0 mmol) in anhyd. Et$_2$O (100 mL) was added, dropwise, under N$_2$, perfluoropropyl iodide (7.6 mL, 48.0 mmol, from Aldrich). To this mixture methyllithium-lithium bromide complex (28.5 mL, 42.0 mmol) was added at a rate which maintained an internal reaction temperature below −70° C. The reaction mixture was stirred at −78° C. for 1 h, the cold bath removed and stirring continued 5 min. The mixture was then poured into H$_2$O (100 mL) and the aqueous phase was acidified with 1 N HCl. The aqueous phase was extracted with additional Et$_2$O (100 mL) and the combined ethereal extracts dried (MgSO$_4$). The solvent was removed in vacuo to yield a crude yellow oil which was immediately flash chromatographed (4.0×25 cm column eluted with 3:1 Et$_2$O-hexane) to give the desired product (MDL 105,731) (493 mg, 9%) as a white foam; FT-IR (KBr) 3421, 3292, 2972, 2937, 2879, 2773, 1755, 1687, 1637, 1525, 1444, 1392, 1367, 1309, 1238, 1174, 1138, 1093, 1043, 1016, 960, 927, 875, 848, 744, 709, 690, 667, 653, 632, 599, 574 cm$^{-1}$; $^{13}$C NMRδ 173.0, 170.9, 155.7, 79.7, 77.2, 77.1, 76.9, 76.6, 59.7, 59.3, 56.8, 47.8, 31.3, 28.9, 28.3, 26.7, 25.1, 19.8, 19.5, 17.4, 16.2; $^{19}$F NMR (376.2 MHz, CDCl$_3$)δ −81.35 (s, CF$_3$), −118.27 and −119.91 (AB quartet, J=297 Hz, CF$_2$), −123.09 (s, CF$_2$), −125.97 (S, CF$_2$); MS (CI/CH$_4$) m/z (rel. intensity) 616 (MH$^+$, 68), 560 (100), 516 (31). Anal. Calcd. for C$_{24}$H$_{34}$F$_9$N$_3$O$_5$: C, 46.83; H, 5.57; N, 6.83. Found: C, 46.32; H, 5.65; N, 6.66. HRMS (C$_{24}$H$_{34}$F$_9$N$_3$O$_5$) (M$^+$) calcd 616.2433, obsd 616.2435.

EXAMPLE 5

Preparation of N-L-valyl-N'-[3,3,4,4,5,5,5-heptafluoro-1-(1-methylethyl)-2-oxopentyl]-L-prolinamide

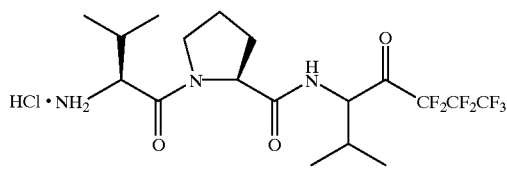

Into a stirred solution of the product of example 3 (0.21 g, 0.37 mmol) in EtOAc (10 mL) cooled in an ice-water bath was bubbled HCl gas for 4 min. The bubbling was ceased and the reaction was stoppered with a drying tube and allowed to warm to ambient temperature with stirring. After 1 h, the reaction was concentrated and azeotroped with CCl$_4$ and placed under a high vacuum to give the desired product (185 mg, 100%) as a white solid; $^1$H NMR (300 MHz, CDCl$_3$)δ 8.29 (br s, 2H, NH$_2$), 7.88 (br s, 1H, NH), 5.70 (m, 1H, CH), 4.89 (m, 1H, CH), 4.16–3.55 (a series of m, 4H, CH, CH, CH$_2$N), 2.40–1.94 (a series of m, 5H, β-CH of Val and CH$_2$CH$_2$), 1.13 (br s, 6H, 2×CH$_3$), 1.01 (d, 3H, J=5.8 Hz, CH$_3$), 0.94 (d, 3H, J=4.8 Hz, CH$_3$); $^{19}$F NMRδ −81.02 (s, CF$_3$), −120.11 (s, CF$_2$), −126.75 (s, CF$_2$).

EXAMPLE 6

Preparation of N-[4-(4-morpholinylcarbonyl)benzoyl]-L-valyl-N'-[3,3,4,4,5,5,5-heptafluoro-1-(1-methylethyl)-2-oxopentyl]-L-prolinamide

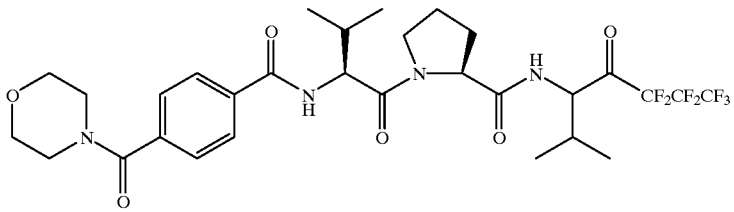

MDL 105,495

To a stirred suspension of 4-(4-morpholinylcarbonyl) benzoic acid (0.13 g, 0.53 mmol) and benzyltriethylammonium chloride (1 mg, 0.004 mmol) in 1,2-dichloromethane (20 mL) was added thionyl chloride (0.05 mL, 0.53 mmol) and the reaction was heated at reflux. After 2.5 h, the reaction was allowed to cool to room temperature and concentrated in vacuo. The residue was then azeotroped with $CCl_4$ and placed under vacuum to give a light orange oil (quantitative) which was used without further purification. In a separate RB flask, a stirred solution of the product of example 5 (185 mg, 0.37 mmol) in $CH_2Cl_2$ (10 mL) was cooled to $-20°$ C. NMM (0.2 mL, 2.0 mmol) was added and imediately followed by the dropwise addition of the acid chloride in $CH_2Cl_2$ (5 mL) at such a rate as to maintain the internal reaction temperature at $-10°$ C. or less. After the addition was complete, the reaction mixture was allowed to warm to room temperature. After 1.5 h at room temperature, the reaction mixture was diluted with $CH_2Cl_2$ (20 mL) and washed with 1N HCl (2×20 mL), saturated $NaHCO_3$ (2×20 mL) and brine (1×20 mL). Drying ($MgSO_4$) and conc. in vacuo afforded a crude form of the desired product (260 mg). The crude white foam was immediately flash chromatographed (2×15 cm column eluted with 1:27 MeOH—$CH_2Cl_2$) to give the desired product (MDL 105,495) (162 mg, 64%) as a white foam; IR (KBr) 3431, 3323, 3049, 2970, 2935, 2877, 1755, 1693, 1631, 1529, 1437, 1394, 1346, 1300, 1278, 1259, 1232, 1161, 1118, 1068, 1014, 933, 896, 862, 842, 798, 785, 740, 686, 653, 628, 596 $cm^{-1}$; $^1H$ NMR (300 MHz, $CDCl_3$) δ 7.86 (d, 2H, J=8.4 Hz, aryl), 7.52 (d, 1H, J=8.4 Hz, NH), 7.46 (d, 2H, J=8.3 Hz, aryl), 7.12 (d, 1H, J=8.7 Hz, NH), 5.04 (dd, 1H, J=8.2, 4.2 Hz, α-CH of Val), 4.84 (dd, 1H, J=8.6, 7.3 Hz, α-CH of Val), 4.62 (dd, 1H, J=7.9, 2.9 Hz, CH of Pro), 3.94–3.37 (m, 10H, 2×$NCH_2CH_2O$ and $NCH_2$ of Pro), 2.29–1.97 (series of m, 6H, 2×β-CH of Val and $CH_2CH_2$), 1.06 (d, 3H, J=6.8 Hz, $CH_3$), 1.01 (d, 6H, J=6.7 Hz, 2×$CH_3$), 0.86 (d, 3H, J=6.9 Hz, $CH_3$); $^{13}C$ NMR δ 172.2, 170.9, 169.2, 166.3, 138.5, 135.1, 127.4, 127.3, 77.4, 77.1, 76.9, 76.5, 66.7, 59.9, 59.3, 55.9, 47.9, 31.8, 29.1, 27.0, 25.1, 19.8, 19.5, 17.8, 16.2; $^{19}F$ NMR (470.2 MHz, $CDCl_3$) δ −80.24 (t, J=9 Hz, $CF_3$), −118.39 and −119.87 (dq, J=295, 9 Hz, $COCF_2$), −125.99 (AB m, $CF_2$); MS ($CI/CH_4$) m/z (rel. intensity) 683 ($MH^+$, 59), 367 (100). Anal. Calcd. for $C_{30}H_{37}F_7N_4O_6$·1.3 $H_2O$: C, 51.01; H, 5.65; N, 7.92. Found: C, 51.34; H, 5.27; N, 7.87.

EXAMPLE 7

Preparation of Boc-Val-$CF_2CF_3$

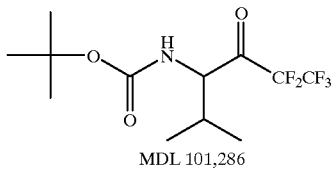

MDL 101,286

A solution of Boc-Val-$OCH_3$ (2.27 g, 9.81 mmol) in $Et_2O$ (14 mL)/PhMe (11.3 mL) was cooled to $-50°$ C. and treated with $CF_3CF_2I$ (3.7 mL, 31.1 . mmol, 3.2 eq), then further cooled to $-60°$ C. and treated dropwise with methyllithium-lithium bromide complex (55 min, $-60°$ C. to $-50°$ C.; 1.5 M in $Et_2O$, 20 mL, 30 mmol, 3.1 eq). The resulting reaction mixture was stirred for 1 h, then treated dropwise with isopropanol (20 min; <−50° C.). After stirring for 30 min, the reaction mixture was allowed to warm to 0° C. then poured into 1 M $KHSO_4$ (60 mL). Phases were separated and the aqueous phase extracted with $Et_2O$ (1×50 mL). The organic phases were combined and dried ($MgSO_4$), filtered and the filtrate evaporated in vacuo (room temperature, 15 mmHg) to provide a white solid. The crude material showed a ratio of desired product to starting material of 3:1 with no other impurity >1% total area (GC). The crude white solid was chromatographed on $SiO_2$ (40 g, 3×6.5 cm; hexane (400 mL) then 400 mL of 10% EtOAc/hexane) to provide 2.22 g, 70% yield, of the desired product. This solid was recrystallized from hexane (40 mL, reflux then cooled to 0° C.) provided 1.62 g, 57%, of pure desired product (MDL 101, 286) (first crop; remaining material in the mother liquor); $R_f$=0.77 in 20% EtOAc/hexane; Mp 69–70° C.; 1H NMR ($CDCl_3$) 5.0 (m, 1H), 4.8 (m, 1H), 2.3 (m, 1H), 1.44 (s, 9H), 1.1 (d, 3H, J=6.8 Hz), 0.84 (d, 3H, J=6.9 Hz); $^{19}F$ NMR ($CDCl_3$) −82.1 (s), −121.4 (d, J=297 Hz), −122.8 (d, J=297 Hz); IR ($CHCl_3$) vmax 3443, 2976, 1753, 1716, 1500, 1369, 1234, 1197, 1163 $cm^{-1}$; UV (MeOH) λmax 225 nm (ε=754); CIMS ($CH_4$) m/e (% relative intensity) 320 ($M^+H^+$, 100). Anal. Calcd. for $C_{12}H_{18}NO_3F_5$: C, 45.14; H, 5.68; N, 4.39. Found: C, 45.28; H, 5.71; N, 4.26.

EXAMPLE 8

Alternative Preparation of Boc-Val-CF$_2$CF$_3$

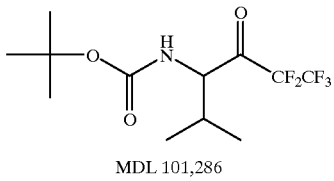

MDL 101,286

A mixture of 288.0 g (1.11 mol) of Boc-Val N-methyl-O-methyl hydroxamic acid and 4.7L of anhydrous Et$_2$O was charged to a 12-L 3-necked flask fitted with a stirrer, thermometer, dry ice condenser, gas dispersion tube and continuous N$_2$ purge. The resulting solution was cooled to −60° C. to −65° C. A total of 885.2 g (3.60 mol) of C$_2$F$_5$I was added via a gas dispersion tube over about 30 min to the solution of Boc-Val N-methyl-O-methyl hydroxamic acid while maintaining a temperature of about −65° C. Immediately upon completing the gas addition, a total of 2.39L of 1.5M CH$_3$Li.LiBr in Et$_2$O (3.59 mol) was added over 1h maintaining a reaction temperature of −52° C. to −58° C. A precipitate formed after about ⅓ of the CH$_3$Li.LiBr had been added but a complete solution was present at the end of the addition. The resulting solution was stirred at −52° C. to −58° C.1 for 1 h. The reaction was monitored by GC (R$_t$ of MDL 101,286=1.3 min, R$_t$ of Boc-Val N-methyl-O-methyl hydroxamic acid=5.1 min) and found to contain 7.2% of Boc-Val N-methyl-O-methyl hydroxamic acid. A total of 255 mL (3.47 mol) of acetone was added over about 15 min maintaining a reaction temperature of −52° C. to −58° C. and the resulting mixture was stirred for 10 min. The mixture was quenched into a 22L flask containing 4.7L of 0.75M KHSO$_4$ which had been cooled to about 0° C. The organic layer was separated and washed with 3L of H$_2$O. The organic layer was dried using 500 g of MgSO$_4$ and filtered to remove the drying agent. The filtrate was concentrated at 40° C./100 torr to a semi-solid weiging 409 g. The crude material was dissolved in 1.2L of hexane at 45° C. and cooled slowly over about 30 min to −25° C. to −30° C. The solid which crystallized was filtered off and washed with 250 mL of hexane at −30° C. The MDL 101,286 obtained was vacuum dried (25° C./100 torr) to give 176.7 g. The filtrate was concentrated at 35° C./100 torr to a residue weighing 153.5 g. The material was put on a Kugelrohr distillation apparatus and a forerun was collected up to 40° C./0.6 torr. The receiver was changed and a total of 100.5 g of crude MDL 101,286 was collected at 40° C.–60° C./0.6 torr. The crude product was dissolved in 500 mL of hexane at about 50° C. The resulting solution was cooled to −30° C. The solid which crystallized was filtered off and washed with 100 mL of cold (−30° C.) hexane. The product was vacuum dried at 25° C./100 torr to give another 68.09 of MDL 101,286 for a total yield of 244.7 g (70% yield) which was 99.9% pure by GC.

Anal. Calcd. for C$_{12}$H$_{18}$F$_5$NO$_3$ (319.28): C, 45.14, H, 5.68, N, 4.39; Found: C, 45.30, 45.49, H, 5.50, 5.58, N, 4.26, 4.35.

EXAMPLE 9

N-[3-(3-pyridyl)propanoyl]-L-valyl-N-[3,3,4,4,4-pentafluoro-1-(1-methylethyl)-2-oxobutyl]-L-prolinamide

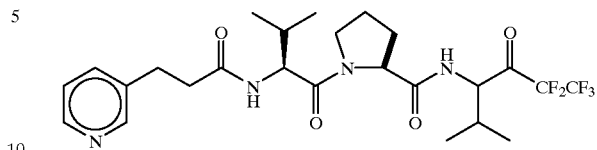

a) Preparation of H-Val-CF$_2$CF$_3$.hydrochloride

Dissolve Boc-Val-CF$_2$CF$_3$ (350 mg, 1.1 mmol) in ethyl acetate (50 mL) and cool to 0° C. Treat with hydrogen chloride gas for 5 minutes and stir for 30 minutes. Remove the solvent in vacuo to give the title compound.

b) Preparation of Boc-Val-Pro-Val-CF$_2$CF$_3$

Dissolve Boc-Val-Pro-OH (314 mg, 1.0 mmol) in methylene chloride (4 mL) and add N-methylmorpholine (252 mg, 2.5 mmol). Cool to −22° C. and add isobutylchloroformate (136 mg, 1.0 mmol). Stir for 20 minutes and add to H-Val-CF$_2$CF$_3$.hydrochloride (1.1 mmol). Stir for 1 hour at −22° C., allow to warm to room temperature and stir for 3 hours. Purify by silica gel chromatography (40% ethyl acetate/hexane) to give the title compound (405 mg).

c) Preparation of H-Val-Pro-Val-CF$_2$CF$_3$.hydrochloride

Dissolve Boc-Val-Pro-Val[CF$_2$CF$_3$] (385 mg, 0.74 mmol) in ethyl acetate (50 mL) and cool to 0° C. Treat with hydrogen chloride gas for 5 minutes and stir for 30 minutes. Evaporate the solvent in vacuo to give the title compound (334 mg).

d) Preparation of N-[3-(3-pyridyl)propanoyl]-L-valyl-N-[3,3,4,4,4-pentafluoro-1-(1-methylethyl)-2-oxobutyl]-L-prolinamide Suspend 3-(3-pyridyl)propionic acid (174 mg, 1.15 mmol, Walker, F. A. et al., *J. Amer. Chem. Soc.*, 102, 5530–5538 (1980)) in methylene chloride (15 mL). Add N-methylmorpholine (0.38 mL, 3.45 mmol) and triethylamine (0.32 mL, 2.30 mmol), and cool the resulting clear, colorless solution to −18° C. Add isobutylchloroformate (0.15 mL, 1.15 mmol) and stir for 20 minutes. Subsequently add N-methylmorpholine (0.13 mL, 1.15 mmol) and H-Val-Pro-Val-CF$_2$CF$_3$.hydrochloride (520 mg, 1.15 mmol) and stir at −20° C. for 1 hour. Allow reaction mixture to warm to room temperature, dilute the reaction mixture with additional methylene chloride (35 mL) and successively wash with 1N HCl (3×20 mL), saturated NaHCO$_3$ (2×20 mL), and brine (1×20 mL). Dry and concentrate the crude product. Purify the crude product by flash chromatography (75:25::acetone:EtOAc) to give the title compound as a white solid foam. (Yield: 470 mg, 74%, 3:1::LLL:LLD).

TLC R$_f$ 0.42 (3:1::acetone:EtOAc); $^1$H NMRδ 8.49 (br s, 1H, aryl), 8.45 (br d, 1H, J=4.2 Hz, aryl), 7.84 (br d, ¼H, J=7.7 Hz, NH), 7.53 (dt, 1H, J=7.8, 1.7 Hz, aryl), 7.50 (br d, ¾H, NH), 7.21 (dd, 1H, i 7.7, 4.8 Hz, aryl), 6.31 (br d, ¾H, J=8.9 Hz, NH), 6.24 (br d, ¼H, J=8.9 Hz, NH), 5.02–4.92 (m, 1H, CH), 4.67 (dd, ¼H, J=8.1, 2.1 Hz, α-CH of Pro), 4.63–4.55 (m, 1¾H, α-CH of Pro and α-CH of Val), 3.87–3.72 and 3.70– 3.55 (pr m, 2H, CH$_2$N), 3.07–2.87 and 2.63–2.50 (pr m, 4H, aryl CH$_2$CH$_2$CO), 2.50–1.80 (m, 6H, 2×β-CH and CH$_2$CH$_2$), 1.12–0.79 (series of d, 12H, 4×CH$_3$), $^{19}$F NMRδ −82.13 (s, CF$_3$, major isomer), −82.17 (s, CF$_3$, minor isomer), −121.53 and −122.71 (AB quartet, J=295 Hz, CF$_2$, minor isomer), −121.59 and −122.61 (AB quartet, J=295 Hz, CF$_2$, major isomer); MS (EI) m/z (rel intensity) 548 (M$^+$, 4), 401 (6), 233 (65), 205 (100), 134 (45), 106 (35), 70 (77).

Anal. (C$_{25}$H$_{33}$F$_5$N$_4$O$_4$.3H$_2$O) C,H,N.

EXAMPLE 10
N-[3-(3-pyridyl)propanoyl]-L-valyl-N-[3,3,4,4,5,5,5-heptafluoro-1-(1-methylethyl)-2-oxopentyl]-L-prolinamide

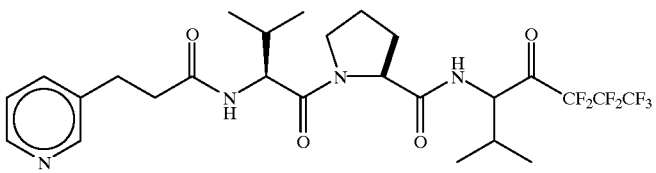

a) Preparation of Boc-Val-Pro-Val-OCH$_3$

Add isobutylchloroformate (1.30 mL, 0.01 mol) to a solution of Boc-Val-Pro-OH (3.1 g, 0.01 mol, Advanced ChemTech) in methylene chloride (100 mL) at −20° C. and stir for 20 minutes. Add an additional equivalent of N-methylmorpholine (1.01 mL, 0.01 mol). Add L-valine methyl ester hydrochloride (1.67 g, 0.01 mol, Aldrich) as a solid in one portion. Stir the reaction mixture at −20° C. for an additional 1 hour and then allow to warm to room temperature. Dilute with additional methylene chloride (50 mL) and wash with 1N HCl (3×50 mL), saturated NaHCO$_3$ (2×50 mL) and brine (1×50 mL). Dry (MgSO$_4$) the resulting organic extract and concentrate in vacuo to afford the title compound as a white foam. (Yield: 4.27 g, 100%). TLC R$_f$ 0.33 (3:1 Et$_2$O-hexane); FT-IR (KBr) 3553, 3537, 3520, 3510, 3310, 2968, 2935, 2876, 1741, 1687, 1631, 1527, 1440, 1390, 1367, 1338, 1309, 1244, 1203, 1172, 1114, 1093, 1043, 1016, 962, 923, 883, 831, 754, 665, 628, 603 cm$^{-1}$; $^1$H NMR (300 MHz, CDCl$_3$)δ 7.22 (br d, 1H, J=8.4 Hz, NH), 5.24 (br d, 1H, J=11.0 Hz, NH), 4.62 (dd, 1H, J=8.2, 2.9 Hz, CH of Val), 4.43 (app. dd, 1H, J=8.6, 5.1 Hz, CH of Pro), 4.30 (dd, 1H, J=9.5, 6.4 Hz, CH of Val), 3.75–3.70 and 3.63–3.59 (pr m, 2H, CH$_2$N), 3.74(s, 3H, OMe), 2.36 (m, 1H, β-CH of Val), 2.17–1.91 (m, 5H, CH$_2$CH$_2$ and β-CH of Val), 1.43 (s, 9H, t-Bu), 1.00 (d, 3H, J=6.7 Hz, CH$_3$), 0.95–0.90 (m, 9H, 3×CH$_3$); $^{13}$C CMRδ 172.5, 172.1, 170.9, 155.8, 79.5, 77.4, 77.1, 76.9, 76.8, 76.5, 59.9, 57.5, 56.7, 52.0, 47.6, 31.4, 31.0, 28.3, 28.2, 27.1, 25.1, 19.5, 18.9, 17.8, 17.3; MS (CI/CH$_4$) m/z (rel intensity) 428 (MH$^+$, 22), 372 (68), 328 (100). Anal. Calcd. for C$_{21}$H$_{37}$N$_3$O$_6$: C, 58.99; H, 8.72; N, 9.83. Found: C, 58.68; H, 8.79; N, 9.55.

b) Preparation of Boc-Val-Pro-Val-CF$_2$CF$_2$CF$_3$

Add perfluoropropyl iodide (6.6 mL, 48.0 mmol, from Aldrich, stabilized with Cu) dropwise, under N$_2$, to a −78° C. solution of Boc-Val-Pro-Val-OCH$_3$] (3.89, 9.0 mmol) in anhydrous diethyl ether (100 mL). Add methyllithium-lithium bromide complex (28.5 mL, 42.0 mmol) at a rate which maintains an internal reaction temperature below −70° C. Stir the reaction mixture at −78° C. for 1 hour, then remove the cold bath and continue stirring for 5 minutes. Pour the reaction mixture into H$_2$O (100 mL) and acidify the aqueous phase with 1N HCl. Extract the aqueous phase with additional diethyl ether (100 mL) and dry (MgSO$_4$) the combined ethereal extracts. Remove the solvent in vacuo and purify the resultant yellow foam by flash chromatography (4.0×25 cm column eluted with 3:1 Et$_2$O-hexane) to yield the title compound as a white foam. (Yield: 654 mg, 13%). FT-IR (KBr) 3423, 3292, 2972, 2937, 2879, 2823, 2771, 2739, 2253, 1755, 1687, 1635, 1525, 1444, 1392, 1367, 1348, 1313, 1232, 1178, 1126, 1041, 1018, 966, 922, 910, 877, 837, 798, 756, 736, 667, 650, 632, 596 cm$^{-1}$; $^1$H NMR (300 MHz, CDCl$_3$)δ 7.63 (d, 1H, J=8.2 Hz, NH), 5.44 (d, 1H, J=9.2 Hz, NH), 5.02 (dd, 1H, J=7.8, 4.5 Hz, CH of Val), 4.64 (dd, 1H, J=8.0, 3.0 Hz, CH of Pro), 4.30 (dd, 1H, J=9.2, 6.8 Hz, α-CH of Val), 3.80–3.74 and 3.66–3.60 (pr m, 2H, CH$_2$N), 2.31–1.92 (series of m, 6H, β-CH of Val, CH$_2$CH$_2$), 1.44 (s, 9H, t-Bu), 1.02 (d, 3H, J=7.0 Hz, CH$_3$), 0.98,(d, 3H, J=6.9 Hz, CH$_3$), 0.94 (d, 3H, J=6.7 Hz, CH$_3$), 0.88 (d, 3H, J=6.9 Hz, CH$_3$); $^{13}$C NMRδ 193.3, 193.0, 192.7, 172.9, 171.1, 155.7, 118.7, 115.8, 111.3, 108.9, 108.6, 108.2, 105.9, 79.6, 77.3, 77.2, 76.9, 76.6, 59.7, 59.3, 56.8, 47.8, 31.4, 29.0, 28.3, 26.9, 25.1, 19.9, 19.8, 19.7, 19.5, 19.4, 17.5, 17.4, 16.3, 16.1; $^{19}$F NMR (376.3 MHz, CDCl$_3$)δ −80.91 (t, CF$_3$), −119.03 and −120.43 (AB quartet, J=297 Hz, CF$_2$), −126.62 (s, CF$_2$), MS (CI/CH$_4$) m/z (rel. intensity) 566 (MH$^+$, 100). HRMS (C$_{23}$H$_{34}$F$_7$N$_3$O$_5$) (M$^+$) calcd 566.2492, obsd 566.2475.

c) Preparation of H-Val-Pro-Val-CF$_2$CF$_2$CF$_3$.hydrochloride

Bubble HCl gas into a stirred solution of Boc-Val-Pro-Val-CF$_2$CF$_2$CF$_3$ (0.21 g, 0.37 mmol) in ethyl acetate (50 mL) and cool in an ice water bath. Treat with hydrogen chloride gas for 4 minutes. Stir the reaction mixture for 1 hour and warm to ambient temperature. Concentrate the reaction mixture and azeotrope with CCl$_4$. Place under a high vacuum to give the title compound as a white solid. (Yield: 185 mg, 100%).

$^1$H NMR (300 MHz, CDCl$_3$)δ 8.29 (br s, 2H, NH$_2$), 7.88 (br s, 1H, NH), 5.70 (m, 1H, CH), 4%89 (m, 1H, CH), 4.16–3.55 (a series of m, 4H, CH, CH, CH$_2$N), 2.40–1.94 (a series of m, 5H, β-CH of Val and CH$_2$CH$_2$), 1.13 (br S, 6H, 2×CH$_3$), 1.01 (d, 3H, J=5.8 Hz, CH$_3$), 0.94 (d, 3H, J=4.8 Hz, CH$_3$); $^{19}$F NMRδ −81.02 (s, CF$_3$), −120.11 (s, CF$_2$), −126.75 (s, CF$_2$).

d) Preparation of 3-(3-pyridyl)propanoyl chloride

Add thionyl chloride (0.05 mL, 0.53 mmol) to a stirred suspension of 3-(3-pyridyl)propionic acid (80.2 mg, 0.53 mmol) and benzyltriethylammonium chloride (1 mg, 0.004 mmol) in 1,2-dichloroethane (20 mL) and heat to reflux for 2.5 hours. Cool the reaction mixture to room temperature and concentrate in vacuo. Azeotrope the residue with CCl$_4$ and place under vacuum. Use the resulting acid chloride without further purification.

e) Preparation of N-[3-(3-pyridyl)propanoyl]-L-valyl-N-[3,3,4,4,5,5,5-heptafluoro-1-(1-methylethyl)-2-oxopentyl]-L-prolinamide Dissolve H-Val-Pro-Val-CF$_2$CF$_2$CF$_3$.hydrochloride (185 mg, 0.37 mmol) in methylene chloride (10 mL) and cool to −20° C. while stirring. Add N-methylmorpholine (0.2 mL, 2.0 mmol) and immediately follow with a dropwise addition of 3-(3-pyridyl)propanoyl chloride in methylene chloride (5 mL) at such a rate as to maintain the internal reaction temperature at −10° C. or less. After completion of the addition, allow the reaction mixture to warm to room temperature. After 1.5 hours at room temperature, dilute the reaction mixture with methylene chloride (20 mL) and wash with 1N HCl (2×20 mL), saturated NaHCO$_3$ (2×20 mL) and brine (1×20 mL). Dry (MgSO$_4$) and concentrate in vacuo to give the title product in crude form. Immediately purify the crude product by flash chromatograpy (2×15 cm column eluted with 1:27 MeOH—CH$_2$Cl$_2$) to give the title compound.

EXAMPLE 11
N-[3-(3-pyridyl)propanoyl]-L-valyl-N-[3,3,4,4,5,5,6,6,6-nonafluoro-1-(1-methylethyl)-2-oxohexyl]-L-prolinamide

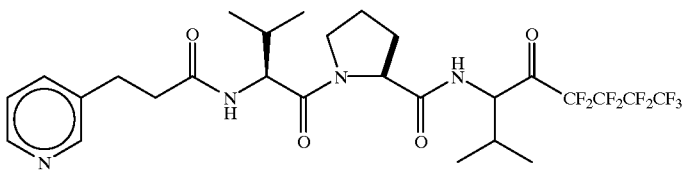

a) Preparation of Boc-Val-Pro-Val [$CF_2CF_2CF_2CF_3$]

Add perfluorobutyl iodide (7.6 mL, 48.0 mmol, from Aldrich) dropwise, under $N_2$, to a −78° C. solution of Boc-Val-Pro-Val [$CO_2CH_3$] (3.8 g, 9.0 mmol) in anhydrous diethyl ether (100 mL). Add methyllithium.lithium bromide complex (28.5 mL, 42.0 mmol) at a rate which maintains an internal reaction temperature below −70° C. Stir the reaction mixture at −78° C. for 1 hour, then remove the cold bath and continue stirring for 5 minutes. Pour the reaction mixture into $H_2O$ (100 mL) and acidify the aqueous phase with 1N HCl. Extract the aqueous phase with additional diethyl ether (100 mm) and dry ($MgSO_4$) the combined ethereal extracts. Remove the solvent in vacuo and purify the resultant yellow cude oil by flash chromatography (4.0×25 cm column eluted with 3:1 $Et_2O$-hexane) to yield the title compound as a white foam. (Yield: 493 mg, 9%).

FT-IR (KBr) 3421, 3292, 2972, 2937, 2879, 2773, 1755, 1687, 1637, 1525, 1444, 1392, 1367, 1309, 1238, 1174, 1138, 1093, 1043, 1016, 960, 927, 875, 848, 744, 709, 690, 667, 653, 632, 599, 574 cm$^{-1}$; $^{13}C$ NMRδ 173.0, 170.9, 155.7, 79.7, 77.2, 77.1, 76.9, 76.6, 59.7, 59.3, 56.8, 47.8, 31.3, 28.9, 28.3, 26.7, 25.1, 19.8, 19.5, 17.4, 16.2; $^{19}F$ NMR (376.2 MHz, $CDCl_3$)δ −81.35 (s, $CF_3$), −118.27 and −119.91 (AB quartet, J=297 Hz, $CF_2$), −123.09 (s, $CF_2$), −125.97 (s, $CF_2$); MS (CI/$CH_4$) m/z (rel. intensity) 616 ($MH^+$, 68), 560 (100), 516 (31). Anal. Calcd. for $C_{24}H_{34}F_9N_3O_5$: C: 46.83; H, 5.57: N, 6.83. Found: C, 46.32; H, 5.65; N, 6.66. HRMS ($C_{24}H_{34}F_9N_3O_5$) ($M^+$) calcd 616.2433, obsd 616.2435.

b) Preparation of H-Val-Pro-Val-$CF_2CF_2CF_2CF_3$.hydrochloride

Bubble HCl gas into a stirred solution of Boc-Val-Pro-Val-$CF_2CF_2CF_2CF_3$ (245 mg, 0.40 mmol) in ethyl acetate (50 mL) and cool in an ice water bath. Treat with hydrogen chloride gas for 4 minutes. Stir the reaction mixture for 1 hour and warm to ambient temperature. Concentrate the reaction mixture and azeotrope with $CCl_4$. Place under a high vacuum to give the title compound.

c) Preparation of N-[3-(3-pyridyl)propanoyl]-L-valyl-N-[3,3,4,4,5,5,6,6,6-nonafluoro-1-(1-methylethyl)-2-oxohexyl]-L-prolinamide Dissolve H-Val-Pro-Val-$CF_2CF_2CF_2CF_3$.hydrochloride (221.0 mg, 0.40 mmol) in methylene chloride (10 mL) and cool to −20° C. while stirring. Add N-methylmorpholine (0.2 mL, 2.0 mmol) and immediately follow with a dropwise addition of 3-(3-pyridyl)propanoyl chloride in methylene chloride (5 mL) at such a rate as to maintain the internal reaction temperature at −10° C. or less. After completion of the addition, allow the reaction mixture to warm to room temperature. After 1.5 hours at room temperature, dilute the reaction mixture with methylene chloride (20 mL) and wash with 1N HCl (2×20 mL), saturated $NaHCO_3$ (2×20 mL) and brine (1×20 mL). Dry ($MgSO_4$) and concentrate in vacuo to give the title product in crude form. Immediately purify the crude product by flash chromatograpy (2×15 cm column eluted with 1:27 MeOH—$CH_2Cl_2$) to give the title compound.

In a further embodiment, the present invention provides a method for the treatment of a patient afflicted with a neutrophil associated inflammatory disease comprising the administration thereto of a therapeutically effective amount of a compound of formulae (I)–(IV). The term "neutrophil associated inflammatory disease" refers to diseases or conditions characterized by the migration of neutrophils to the site of inflammation and its participation in proteolytic degradation of biological matrices. Neutrophil associated inflammatory diseases for which treatment with a compound of formulae (I)–(IV) will be particularly useful include: emphysema, cystic fibrosis, adult respiratory distress syndrome, septicemia, chronic bronchitis, inflammatory bowel disease (particularly ulcerative colitis or Crohn's disease), disseminated intravascular coagulation, gout and rheumatoid arthritis. Compounds of formulae (I)–(IV) which are particularly preferred for the treatment of neutrophil associated inflammatory diseases include:

N-[4-(4-morpholinylcarbonyl)benzoyl]-L-valyl-N'-[3,3,4,4,5,5,5-heptafluoro-1-(1-methylethyl)-2-oxopentyl]-L-prolinamide;

N-[4-(4-morpholinylcarbonyl)benzoyl]-L-valyl-N'-[3,3,4,4,5,5,6,6,6-nonafluoro-1-(1-methylethyl)-2-oxohexyl]-L-prolinamide;

N-[(1,1-dimethylethoxy)carbonyl]-L-valyl-N'-[3,3,4,4,5,5,5-heptafluoro-1-(1-methylethyl)-2-oxopentyl]-L-prolinamide;

N-[(1,1-dimethylethoxy)carbonyl]-L-valyl-N'-[3,3,4,4,5,5,6,6,6-nonafluoro-1-(1-methylethyl)-2-oxohexyl]-L-prolinamide;

N-[3-(3-pyridyl)propanoyl]-L-valyl-N'-[3,3,4,4,4-pentafluro-1-(1-methylethyl)-2-oxobutyl]-L-prolinamide;

N-[3-(3-pyridyl)propanoyl]-L-valyl-N'-[3,3,4,4,4-pentafluoro-1-(1-methylethyl)-2-oxobutyl]-D,L-1,2,3,4-tetrahydro-3-isoquinolinamide;

N-[3-(3-pyridyl)propanoyl]-L-valyl-N'-[3,3,4,4,4-pentafluro-1-(1-methylethyl)-2-oxobutyl]-L-thiazolidine-4-carboxylic acid.

As used herein, the term "patient" refers to a warm blooded animal such as a mammal which is afflicted with a particular inflammatory disease state. It is understood that guinea pigs, dogs, cats, rats, mice, horses, cattle, sheep, and humans are examples of animals within the scope of the meaning of the term.

The term "therapeutically effective amount" refers to an amount which is effective, upon single or multiple dose administration to the patient, in providing relief of symptoms associated with neutrophil associated inflammatory diseases. As used herein, "relief of symptoms" of a respiratory disease refers to a decrease in severity over that expected in the absence of treatment and does not necessarily indicate a total elimination or cure of the disease. In determining the therapeutically effective amount or dose, a number of factors are considered by the attending diagnostician, including, but not limited to: the species of mammal; its size, age, and general health: the specific disease involved; the degree of or involvement or the severity of the disease; the response of the individual patient; the particular compound administered; the mode of administration; the bioavailability characteristics of the preparation administered; the dose regimen selected; the use of concomitant medication; an: other relevant circumstances.

A therapeutically effective amount of a compound of formulae (I)–(IV) is expected to vary from about 0.1 milligram per kilogram of body weight per day (ng/kg/day) to about 100 mg/kg/day. Preferred amounts are expected to vary from about 0.5 to about 10 mg/kg/day.

The compounds of this invention are highly potent inhibitors of elastase, particularly human neutrophil elastase. It is believed that the compounds of this invention exert their inhibitory effect through inhibition of the enzyme elastase and thereby provide relief for elastase-mediated diseases including but not limited to emphysema, cystic fibrosis, adult respiratory distress syndrome, chronic bronchitis, inflammatory bowel disease, septicemia, disseminated intravascular coagulation, gout and rheumatoid arthritis. However, it is understood that the present invention is not limited by any particular theory or proposed mechanism to explain its effectiveness in an end-use application.

In effecting treatment of a patient afflicted with a disease state described above, a compound of formulae (I)–(IV) can be administered in any form or mode which makes the compound bioavailable in effective amounts, including oral, aerosol, and parenteral routes. For example, compounds of formulae (I)–(IV) can be administered orally. by aerosolization, subcutaneously, intramuscularly, intravenously, transdermally, intranasally, rectally, topically, and the like. Oral or aerosol administration is generally preferred. One skilled in the art of preparing formulations can readily select the proper form and mode of administration depending upon the particular characteristics of the compound selected the disease state to be treated, the stage of the disease, and other relevant circumstances. Remington's Pharmaceutical Sciences, 18th Edition, Mack Publishing Co. (1990).

The compounds can be administered alone or in the form of a pharmaceutical composition in combination with pharmaceutically acceptable carriers or excipients, the proportion and nature of which are determined by the solubility and chemical properties of the compound selected, the chosen route of administration, and standard pharmaceutical practice. The compounds of the invention, while effective themselves, may be formulated and administered in the form of their pharmaceutically acceptable salts, such as for example, acid addition salts, for purposes of stability, convenience of crystallization, increased solubility and the like.

In another embodiment, the present invention provides compositions comprising a compound of formulae (I)–(IV) in admixture or otherwise in association with one or more inert carriers. These compositions are useful, for example, as assay standards, as convenient means of making bulk shipments, or as pharmaceutical compositions. An assayable amount of a compound of formulae (I)–(IV) is an amount which is readily measurable by standard assay procedures and techniques as are well known and appreciated by those skilled in the art. Assayable amounts of a compound of formulae (I)–(IV) will generally vary from about 0.001% to about 75% of the composition by weight. Inert carriers can be any material which does not degrade or otherwise covalently react with a compound of formulae (I)–(IV). Examples of suitable inert carriers are water; aqueous buffers, such as those which are generally useful in High Performance Liquid Chromatography (HPLC) analysis; organic solvents, such as acetonitrile, ethyl acetate, hexane and the like: and pharmaceutically acceptable carriers or excipients.

More particularly, the present invention provides pharmaceutical compositions comprising a therapeutically effective amount of a compound of formulae (I)–(IV) in admixture or otherwise in association with one or more pharmaceutically acceptable carriers or excipients.

The pharmaceutical compositions are prepared in a manner well known in the pharmaceutical art. The carrier or excipient may be a solid, semi-solid, or liquid material which can serve as a vehicle or medium for the active ingredient. Suitable carriers or excipients are well known in the art. The pharmaceutical composition may be adapted for oral, parenteral, or topical use and may be administered to the patient in the form of tablets, capsules, suppositories, solution, suspensions, or the like.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compound of the invention, the active ingredient, but may be varied depending upon the particular form and may conveniently be between 4% to about 70% of the weight of the unit. The amount of the compound present in compositions is such that a suitable dosage will be obtained. Preferred compositions and preparations according to the present invention are prepared so that an oral dosage unit form contains between 5.0–300 milligrams of a compound of the invention.

The tablets, pills, capsules, troches and the like may also contain one or more of the following adjuvants: binders such as microcrystalline cellulose, gum tragacanth or gelatin; excipients such as starch or lactose, disintegrating agents such as alginic acid, Primogel, corn starch and the like; lubricants such as magnesium stearate or Sterotex; glidants such as colloidal silicon dioxide; and sweetening agents such as sucrose or saccharin may be added or a flavoring agent such as peppermint, methyl salicylate or orange flavoring. When the dosage unit form is a capsule, it may contain, in addition to materials of the above type, a liquid carrier such as polyethylene glycol or a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations should contain at least 0.1% of a compound cf the invention, but may be varied to be between 0.1 and about 50% of the weight thereof. The amount of the inventive compound present in such compositions is such that a suitable dosage will be obtained. Preferred compositions and preparations according to the present invention are prepared so that a parenteral dosage unit contains between 5.0 to 100 milligrams of the compound of the invention.

The compounds of formulae (I)–(IV) of the present invention may also be administered by aerosol. The term aerosol is used to denote a variety of systems ranging from those of colloidal nature to systems consisting of pressurized packages. Delivery may be by a liquefied or compressed gas or by a suitable pump system which dispenses the active ingredients. Aerosols of compounds of formulae (I)–(IV) may be delivered in single phase, bi-phasic, or tri-phasic systems in order to deliver the active ingredient. Delivery of the aerosol includes the necessary container, activators, valves, subcontainers, and the like. Preferred aerosol are able to be determined by one skilled in the art.

The compounds of formulae (I)–(IV) of this invention may also be administered topically, and when done so the carrier may suitably comprise a solution, ointment or gel base. The base, for example, may comprise one or more of the following: petrolatum, lanolin, polyethylene glycols, bee wax, mineral oil, diluents such as water and alcohol, and emulsifiers and stabilizers. Topical formulations may contain a concentration of the formula 1 or its pharmaceutical salt from about 0.1 to about 10% w/v (weight per unit volume).

The solutions or suspensions may also include one or more of the following adjuvants: sterile diluents such as water for infection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

Human neutrophil elastase is assayed in vitro using N-MeOSuc-Ala-Ala-Pro-Val-p-nitroanilide, available commercially, as substrate. The assay buffer, pH and assay techniques are similar to those described by Mehdi, et al., *Biochemical and Biophysical Research Communications,* 166, 595 (1990). Enzyme is purified from human sputum, although recently it has become commercially available. Kinetic characterization of immediate inhibitors is by means of the Dixon plot, whereas the characterization of slow- and/or tight-binding inhibitors used data analysis techniques reviewed by Williams and Morrison. The synthesis and analytical use of a highly sensitive and convenient substrate of elastase is described in J. Bieth, B. Spiess and C. G. Wermuth, *Biochemical Medicine,* 11 (1974) 350–375. Table 2 summarizes the ability of selected compounds of this invention to inhibit elastase. For the purposes of this table, MCBz refers to 4-(4-morpholinylcarbonyl)benzoyl and Pyr refers to 3-(3-pyridyl)propanoyl.

TABLE 2

| COMPOUND | ENZYME Human Neutrophil Elastase Ki (nM) |
|---|---|
| Boc—Val—Pro—Val—$CF_2CF_2CF_3$ | 490 |
| Boc—Val—Pro—Val—$CF_2CF_2CF_2CF_3$ | 590 |
| MCBz—Val—Pro—Val—$CF_2CF_2CF_3$ | 18 |
| Pyr—Val—Pro—Val—$CF_2CF_3$ | 29 |

Intratracheal instillation of HNE in rodents results in acute lung damage that can easily be quantitated by measuring hemoglobin ("Hgb") in the bronchial lavage fluid ("BAL"); Fletcher, D. S., et al., *Am. Rev. Resp. Dis.* 141, 672–677 (1990). The efficacy of the compounds of formulae (I)–(IV) to decrease pulmonary hemorrhage and/or show inhibition of human neutrophil elastase ("HNE") in vivo can be demonstrated by the pulmonary hemorrhage model in rodents as illustrated in Fletcher, D. S., et al., *Id.* and Shah, S. K., et al., *J. Med. Chem.* 35, 3745–3754 (1992).

For example, hamsters may be pretreated with N-[3-(3-pyridyl)propanoyl]-L-valyl-N'-[3,3,4,4,4-pentafluro-1-(1-methylethyl)-2-oxobutyl]-L-prolinamide ("Pyr-Val-Pro-Val-$CF_2CF_3$") (10, 25 or 50 mg/kg, oral administration) 30 minutes before challenge with HNE (20 μg, intratracheal administration). Animals may be sacrificed 1 hour after challenge. For hamsters given a 25 mg/kg oral dose of Pyr-Val-Pro-Val-$CF_2CF_3$ 30 minutes prior to intratracheal challenge with HNE, a 67±6% inhibition of HNE-induced pulmonary hemorrhage as measured by BAL Hgb was noticed.

What is claimed is:

1. A compound of the formula (SEQ. ID NO. 4)

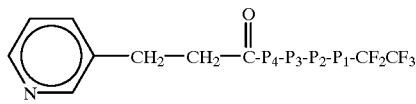

wherein $P_1$ is Ala, Val, Nva, bVal, Leu, Ile or Nle;

$P_2$ is Ala, bAla, Leu, Ile, Val, Nva, bVal, Met, Nle, Gly, Phe, Tyr, Trp, or Nal(1) there the nitrogen of the alpha-amino group can be substituted with an R group where R is a $(C_{1-6})$alkyl, $(C_{3-12})$cycloalkyl, $(C_{3-12})$cycloalkyl$(C_{1-6})$alkyl, $(C_{4-11})$bicycloalkyl, $(C_{4-11})$bicycloalkyl$(C_{1-6})$alkyl, $(C_{6-11})$aryl, $(C_{6-10})$aryl$(C_{1-6})$alkyl, $(C_{3-7})$heterocycloalkyl, $(C_{3-7})$heterocycloalkyl $(C_{1-6})$alkyl, $(C_{5-9})$heteroaryl, $(C_{5-9})$heteroaryl$(C_{1-6})$alkyl, fused $(C_{6-10})$aryl-$(C_{3-12})$cycloalkyl, fused $(C_{6-10})$aryl$(C_{3-12})$cyclo-alkyl$(C_{1-6})$alkyl, fused $(C_{5-9})$heteroaryl$(C_{3-12})$cyclo-alkyl, or fused $(C_{5-9})$heteroaryl $(C_{3-12})$cycloalkyl-$(C_{1-6})$alkyl, or $P_2$ is Pro, Ind, Tic or Tca;

$P_3$ Is Ala, bAla, Leu, Ile, Val, Nva, bVaL or Nle;

$P_4$ is Ala, bAla, Leu, Ile, Val, Nva, bVal, Nle or a bond;

or a hydrate, isostere, or pharmaceutically acceptable salt thereon.

2. A compound of claim 1 wherein $P_1$ is Val or Nva; $P_2$ is Pro, Tic or Tca; $P_3$ is Val, Nva, Ala or bAla; and $P_4$ is Ala or a bond.

3. A compound of claim 2 wherein $P_1$ is Val; $P_3$ is Val and $P_4$ is a bond.

4. A compound of claim 1 wherein the compound is N-[3-(3-pyridyl)propanoyl]-L-valyl-N'-[3,3,4,4,4-pentafluro-1-(1-methylethyl)-2-oxobutyl]-L-prolinamide.

5. A composition comprising a compound of claim 1 and a carrier.

6. A pharmaceutical composition comprising a compound of claim 1 and a pharmaceutically acceptable carrier.

7. A method for inhibiting human neutrophil elastase in a patient in need thereof, said method comprising the administration thereto of a therapeutically effective amount of a compound of claim 1.

8. A method of treating a patient afflicted with a neutrophil associated inflammatory disease, said method comprising the administration thereto of a therapeutically effective amount of a compound of claim 1.

9. A method according to claim 8 wherein said neutrophil associated inflammatory disease is emphysema.

* * * * *

UNITED STATES PATENT AND TRADEMARK OFFICE
CERTIFICATE OF CORRECTION

PATENT NO. : 6,008,196
DATED : December 28, 1999
INVENTOR(S) : Timothy T. Curran et al.

It is certified that error appears in the above-identified patent and that said Letters Patent is hereby corrected as shown below:

Column 1,
Line 31, reads "$P_1$" and should read -- PI --.
Line 32, reads "$P_1$" and should read -- PI --.
Line 40, reads "$SLP_1$" and should read -- SLPI --
Line 43, reads "$\alpha$-1-$P_1$ and $SLP_1$" and should read -- $\alpha$-1-PI and SLPI --.
Line 47, reads "$\alpha$-1-$P_1$" and should read -- $\alpha$-1-PI --.
Line 54, reads "$\alpha$-1-$P_1$" and should read -- $\alpha$-1-PI --.

Column 3,
Line 57, reads "-X(II)" and should read -- -X (II) --.

Column 4,
Line 1, reads "lie," and should read -- Ile, --.
Line 32, reads "i to 6" and should read -- 1 to 6 --.
Line 67, reads "K" is or" and should read -- K" is --.

Column 6,
Line 14, reads "(R,)" and should read -- ($R_1$) --.

Column 7,
Line 16, reads "Linkage" and should read -- linkage --.

Column 11,
Line 19, reads "[3,4" and should read -- [3,3,4, --.
Line 20, reads "-1,(1" and should read -- -1-(1 --.
Line 36, reads "[1(1,1-" and should read -- [ (1,1- --.

Column 12,
Line 47, reads "-N-" and should read -- -N'- --.

UNITED STATES PATENT AND TRADEMARK OFFICE
CERTIFICATE OF CORRECTION

PATENT NO. : 6,008,196
DATED : December 28, 1999
INVENTOR(S) : Timothy T. Curran et al.

It is certified that error appears in the above-identified patent and that said Letters Patent is hereby corrected as shown below:

Column 14,
Line 24, reads "be en" and should red -- been --.
Line 36, reads "A-amine" and should read -- α-amine --.

Column 15,
Line 33, reads "croup" and should read -- group --.
Line 59, reads "dimethlformamide" and should read -- dimethylformamide --.

Column 16,
Line 27, reads "additivies" and should read -- additives --.

Column 17,
Lines 6 and 7, read "wherein (is" and should read -- wherein K is --.
Lines 22 and 23, reads "suitably, suitably" and should read -- suitably --.

Column 22,
Line 21, reads "0°C. room," and should read -- 0°C to room --.

Column 23,
Line 35, reads "ip" and should read -- is --.
Line 36, reads "(17) for (18)]" and should read -- (17) [or (18) ] --.

Column 26,
Line 44, reads "48.0=ol)." and should read -- 48.0 mmol). --.
Line 58, reads "1H, 7.9.2" and should read -- 1H, J = 9.2 --.
Line 59, reads "$C_3$" and should read -- CH --; and reads "1H, 58.1," and should read -- 1H, J = 8.1, --.

Column 27,
Line 26, reads "addition," and should read -- additional --.
Line 45, reads "29.0,29.3," and should read -- 29.0, 28.3, --.

UNITED STATES PATENT AND TRADEMARK OFFICE
CERTIFICATE OF CORRECTION

PATENT NO. : 6,008,196
DATED : December 28, 1999
INVENTOR(S) : Timothy T. Curran et al.

It is certified that error appears in the above-identified patent and that said Letters Patent is hereby corrected as shown below:

Column 28,
Line 1, reads "(3.89," and should read -- (3.8g, --.

Column 31,
Line 61, reads "68.09" and should read -- 68.0g --.

Column 32,
Line 54, reads "i 7.7," and should read -- J = 7.7, --.
Line 67, reads ".3H$_2$O" and should read -- •0.3 H$_2$O) --.

Column 33,
Line 19, reads "(1.01 mL," and should read -- (1.10mL, --.
Line 35, reads "3.74" and should read -- 3.7 --.
Line 49, reads "3.89," and should read -- 3.8g, --.

Column 34,
Line 34, reads "4%89" and should read -- 4.89 --.

Column 35,
Line 25, reads "(100 mm)" and should read -- (100mL) --.
Line 26, reads "cude" and should read -- crude --.

Column 36,
Line 41, reads "pentafluro" and should read -- pentafluoro --.
Line 46, reads "pentafluro" and should read -- pentafluoro --.

UNITED STATES PATENT AND TRADEMARK OFFICE
CERTIFICATE OF CORRECTION

PATENT NO.    : 6,008,196
DATED         : December 28, 1999
INVENTOR(S)   : Timothy T. Curran et al.

It is certified that error appears in the above-identified patent and that said Letters Patent is hereby corrected as shown below:

Column 37,
Line 5, reads "an:" and should read -- and --.
Line 8, reads "(ng/" and should read -- (mg/ --.

Column 39,
Line 14, reads "infection" and should read -- injection --.

Column 43,
Line 13, reads "there the" and should read -- where the --.
Lien 17, reads "($C_6$-$_{11}$)" and should read -- ($C_6$-$_{10}$) --.

Column 44,
Line 2, reads "thereon" and should read -- thereof --.
Line 10, reads "pentafluro" and should read -- pentafluoro --.

Signed and Sealed this

Twelfth Day of March, 2002

Attest:

JAMES E. ROGAN
*Attesting Officer*   *Director of the United States Patent and Trademark Office*

SEQUENCE LISTING

```
(1) GENERAL INFORMATION:

(iii) NUMBER OF SEQUENCES: 7

(2) INFORMATION FOR SEQ ID NO:1:

(i) SEQUENCE CHARACTERISTICS:
          (A) LENGTH: 4 amino acids
          (B) TYPE: amino acid
          (D) TOPOLOGY: linear (ii) MOLECULE TYPE: peptide (xi) SEQUENCE DESCRIPTION: SEQ ID NO:1:

Xaa Xaa Xaa Xaa
1

(2) INFORMATION FOR SEQ ID NO:2:

(i) SEQUENCE CHARACTERISTICS:
          (A) LENGTH: 4 amino acids
          (B) TYPE: amino acid
          (D) TOPOLOGY: linear (ii) MOLECULE TYPE: peptide (xi) SEQUENCE DESCRIPTION: SEQ ID NO:2:
```

-continued

```
Xaa Xaa Xaa Xaa
 1

(2) INFORMATION FOR SEQ ID NO:3:

(i) SEQUENCE CHARACTERISTICS:
         (A) LENGTH: 4 amino acids
         (B) TYPE: amino acid
         (D) TOPOLOGY: linear (ii) MOLECULE TYPE: peptide (xi) SEQUENCE DESCRIPTION: SEQ ID NO:3:

Xaa Xaa Xaa Xaa
 1

(2) INFORMATION FOR SEQ ID NO:4:

(i) SEQUENCE CHARACTERISTICS:
         (A) LENGTH: 4 amino acids
         (B) TYPE: amino acid
         (D) TOPOLOGY: linear (ii) MOLECULE TYPE: peptide (xi) SEQUENCE DESCRIPTION: SEQ ID NO:4:

Xaa Xaa Xaa Xaa
 1

(2) INFORMATION FOR SEQ ID NO:5:

(i) SEQUENCE CHARACTERISTICS:
         (A) LENGTH: 4 amino acids
         (B) TYPE: amino acid
         (D) TOPOLOGY: linear (ii) MOLECULE TYPE: peptide (xi) SEQUENCE DESCRIPTION: SEQ ID NO:5:

Xaa Xaa Xaa Xaa
 1

(2) INFORMATION FOR SEQ ID NO:6:

(i) SEQUENCE CHARACTERISTICS:
         (A) LENGTH: 4 amino acids
         (B) TYPE: amino acid
         (D) TOPOLOGY: linear (ii) MOLECULE TYPE: peptide (xi) SEQUENCE DESCRIPTION: SEQ ID NO:6:

Xaa Xaa Xaa Xaa
 1

(2) INFORMATION FOR SEQ ID NO:7:

(i) SEQUENCE CHARACTERISTICS:
         (A) LENGTH: 4 amino acids
         (B) TYPE: amino acid
         (D) TOPOLOGY: linear (ii) MOLECULE TYPE: peptide (xi) SEQUENCE DESCRIPTION: SEQ ID NO:7:

Xaa Xaa Xaa Xaa
```